US009545396B2

(12) United States Patent
Duan et al.

(10) Patent No.: US 9,545,396 B2
(45) Date of Patent: Jan. 17, 2017

(54) METHOD AND PHARMACEUTICAL COMPOSITION FOR INHIBITING PI3K/AKT/MTOR SIGNALING PATHWAY

(71) Applicant: Targeted Therapeutics, LLC, Buffalo Grove, IL (US)

(72) Inventors: Lei Duan, Evanston, IL (US); Victor Levenson, Buffalo Grove, IL (US); Guoguang Ying, Tianjin (CN)

(73) Assignee: Targeted Therapeutics, LLC, Buffalo Grove, IL (US)

( * ) Notice: Subject to any disclaimer, the term of this patent is extended or adjusted under 35 U.S.C. 154(b) by 0 days.

(21) Appl. No.: 14/431,441

(22) PCT Filed: Sep. 29, 2013

(86) PCT No.: PCT/CN2013/001182
§ 371 (c)(1),
(2) Date: Mar. 26, 2015

(87) PCT Pub. No.: WO2014/048071
PCT Pub. Date: Apr. 3, 2014

(65) Prior Publication Data
US 2015/0328197 A1    Nov. 19, 2015

(30) Foreign Application Priority Data

Sep. 29, 2012   (CN) .......................... 2012 1 0379418

(51) Int. Cl.
| | | |
|---|---|---|
| A01N 43/36 | (2006.01) |
| A61K 31/40 | (2006.01) |
| A61K 31/436 | (2006.01) |
| A61K 31/7105 | (2006.01) |
| A61K 31/4025 | (2006.01) |
| A61K 31/381 | (2006.01) |
| C12N 15/113 | (2010.01) |
| A61K 45/06 | (2006.01) |
| A61K 31/4436 | (2006.01) |
| A61K 31/4439 | (2006.01) |
| A61K 31/7052 | (2006.01) |

(52) U.S. Cl.
CPC ........... *A61K 31/436* (2013.01); *A61K 31/381* (2013.01); *A61K 31/4025* (2013.01); *A61K 31/4436* (2013.01); *A61K 31/4439* (2013.01); *A61K 31/7052* (2013.01); *A61K 31/7105* (2013.01); *A61K 45/06* (2013.01); *C12N 15/1137* (2013.01)

(58) Field of Classification Search
USPC ........................................................ 514/408
See application file for complete search history.

(56) References Cited

U.S. PATENT DOCUMENTS

| | | |
|---|---|---|
| 3,993,749 A | 11/1976 | Sehgal et al. |
| 4,316,885 A | 2/1982 | Rakhit |
| 5,001,137 A | 3/1991 | Oe et al. |
| 5,100,883 A | 3/1992 | Schiehser |
| 5,102,876 A | 4/1992 | Caufield |
| 5,118,667 A | 6/1992 | Adams et al. |
| 5,120,842 A | 6/1992 | Failli et al. |
| 5,130,307 A | 7/1992 | Failli et al. |
| 5,138,051 A | 8/1992 | Hughes et al. |
| 5,151,413 A | 9/1992 | Caufield et al. |
| 5,164,399 A | 11/1992 | Failli et al. |
| 5,233,036 A | 8/1993 | Hughes |
| 5,310,903 A | 5/1994 | Goulet et al. |
| 5,344,833 A | 9/1994 | Hughes |
| 5,346,893 A | 9/1994 | Failli et al. |
| 5,362,718 A | 11/1994 | Skotnicki et al. |
| 5,411,976 A | 5/1995 | Kado et al. |
| 5,446,048 A | 8/1995 | Failli et al. |
| 5,504,091 A | 4/1996 | Molnar-Kimber et al. |
| 5,637,590 A | 6/1997 | Skotnicki et al. |
| 5,922,730 A | 7/1999 | Hu et al. |
| 5,955,457 A | 9/1999 | Lee et al. |
| 6,277,983 B1 | 8/2001 | Shaw et al. |
| 6,399,625 B1 | 6/2002 | Zhu |
| 6,440,990 B1 | 8/2002 | Cottens et al. |
| 6,677,357 B2 | 1/2004 | Zhu et al. |
| 6,680,330 B2 | 1/2004 | Zhu et al. |
| 7,384,953 B2 | 6/2008 | Shaw et al. |

FOREIGN PATENT DOCUMENTS

| | | |
|---|---|---|
| JP | 08034732 | * 2/1996 |
| WO | WO2005115446 | 12/2005 |

(Continued)

OTHER PUBLICATIONS

Kato et. al. (The Journal of Pharmacology and Experimental Therapeutics (1997) 283:328-335).*

(Continued)

*Primary Examiner* — Marcos Sznaidman

(74) *Attorney, Agent, or Firm* — Greer, Burns & Crain, Ltd.

(57) ABSTRACT

The present invention relates to a pharmaceutical composition of PRCP antagonist, PREP antagonist, or PRCP-PREP dual antagonist. The present invention also relates to a pharmaceutical composition jointly using PRCP antagonist and mTOR antagonist, or jointly using PREP antagonist and mTOR antagonist, or jointly using PRCP-PREP dual antagonist and mTOR antagonist. In addition, the present invention also relates to a method for utilizing the pharmaceutical compositions to treat and prevent cancers and diseases related to insulin receptor substrate protein and PI3K/AKT/mTOR signal pathway.

3 Claims, 19 Drawing Sheets

(56) References Cited

FOREIGN PATENT DOCUMENTS

| WO | WO 2007/140896 | * | 12/2007 |
| WO | WO 2011/156220 | * | 12/2011 |

OTHER PUBLICATIONS

Smolewski (Expert Opinion on Investigational Drugs (2006) 15:1201-1227).*
Takahashi et. al. (Biochim. Biophys. Acta. (2011) 1813(8): 1465-1474).*
Tarrago et. al. (Bioorganic and medicinal Chemistry (2008) 16:7516-7524).*
Stephan et. al. (Clinical Cancer Research (2004) 10:6993-7000).*
Arafat H. et al, "Tumor-Specific Expression and Alternative Splicing of the COL6A3 Gene in Pancreatic Cancer" (201 1) Surgery 150 (2), pp. 306-315.
Bergmann et al, "Increased Expression of Insulin Receptor Substrate-1 in Human Pancreatic Cancer" (1996) Biochemical and Biophysical Research Communications 220: pp. 886-890.
Cantley et al. "New Insights Into Tumor Suppression: PTEN Suppresses Tumor Formation by Restraining athe Phosphoinositide 3-Kinase / AKT Pathway" (1999) PNAS 96:4240-4245.
Courtney et al, :The PI3K Pathway as Drug Target in Human Cancer (2010) Journal of Clinical Oncology, vol. 28: 1075-1083.
Duan L. et al, Prolylcarboxypeptidase Regulates Proliferation, Autophagy, and Resistance to 4-Hydroxytamoxifen-induced Cytotoxicity in Estrogen Receptor-positive Breast Cancer Cells, The Joural of Biological Chemistry (2011) vol. 28, pp. 864-2876.
Dearth et al, Mammary Tumorigenesis and Metastasis Caused by Overexpression of Insulin Receptor Substrate 1 (IRS-1) or IRS-2, Molecular and Cellular Biology, (2006) pp. 9302-9314.
Etoh T. et al, "Oncolytic Viral Therapy for Human Pancreatic Cancer Cells by Reovirus" (2003) Clinical Cencer Research, vol. 9; pp. 1218-1223.
Engelman et al, "The Evolution of Phosphatidylinositol 3-kinases as Regulators of Growth and Metabolism" (2006) Nature Reviews Genetics, vol. 7, pp. 606-619.
Engelman, Ja, "Targeting PI3K Signally in Cancer Opportunities, Challenges and Limitations" (2009) Nature Reviews: Cancer vol. 9, pp. 550-551.
Easton et al, "IRS-1: Auditing the Effectiveness of mTor Inhibitors" (2006) Cancer Cell (2006) pp. 153-155.
Garcia-Horsman et al On the Role of Prolyl Oligopeptidase in Health and Disease (2007) Neutopeptides 41: pp. 1-24.
Grunwald et al. Inhibitors of mTor Reverse Doxorubicin Resistance Conferred by PTEN Status in Prostate Cancer Cells, (2002) American Association for Cancer Res. 62: pp. 6141-5145.
Kozma et al, "Regulation of Cell Size in Growth Development and Human Disease: PI3K, PKB, and S6K" (2002) Bioessays 24: pp. 65-71.
Katso et al. Cellular Function of Phosphoinositide 3-Kinases: Implications for Development, Immunity, Homeostatsis, and Cancer (2001) Annu. Rev. Cell Dev. Biol. 17:615-75.
Metz, et al, "Insulin Receptor Substrate Regulation of Phosphoinositide 3-Kinase" (2011) Clinical Cancer Research 17:. 206-21 1.
Manning et al, "AKT/PKB Signaling: Navigating Downsteam" (2007) Cell 129: 1261-1274.
Markman et al., "Status of P13K Inhibition and Biomarker Development in Cancer Therapeutics" (2009) Annals of Oncology 21 (4) :683-91.
Reuveni et al, :Therapeutic Destruction of Insulin Receptor Substrates for Cancer Treatment (2013) Cancer Research 73: 4383-4394.
Rosenblum JS et al "Prolyl Peptidases: a Serine Protease Subfamily with High Potential for Drug Discovery" (2003) Current Opinion in Chemical Biology, 7:496-504.
Richter B. et al, Dipeptidyl Peptidase-4 (DPP-4) Inhibitors for Type 2 Diabetes Mellitus (Review) (2008) The Cochrane Collaboration, (2009), Issue 3.
Rozengurt E. et al, "Crosstalk Between Insulin/Insulin-like Growth Factor-1 Receptors and G Protein-Coupled Receptor Signaling Systems: A Novel Target for the Antidiabetic Drug Metformin in Pancreatic Cancer" American Association for Cancer Research (2010); 16: 2505-11.
Shariat-Madar B. et al, Prolylcarboxpeptidase (PRCP) as a New Targte for Obesity Treatment (2010) Diabetes, Metabolic Syndrome and Obesity: Targets and Therapy, (2010) 3: pp. 67-78.
Skidgel R. et al, "Cellular Carboxypeptidases" (1998) Immunological Reviews, (1998) 161: pp. 129-141.
Stolovich M. et al. "Transduction of Growth or Mitogenic Signals into Translational Activation of TOP mRNAs is Fully Reliant on the Phosphatidylinositol 3-Kinase-Mediated Pathway But Requires Neither S6K1 nor rpS6 Phosphorylation" (2002) Molecular and Cellular Biology, vol. 22, p. 8101.
Copps K. D. et al."Regulation of Insulin Sensitivity by Serine/ Threonine Phosphorylation of Insulin Receptor Substrate Proteins IRS1 and IRS2" (2012). Diabetologia, 55(10) pp. 2565-2582.
Kobari M. et al, "Establishment of Six Human Pancreatic Cancer Cell Lines and Their Sensitivities to Anti-Tumor Durgs" Tohoku J Exp Med. (1986) 150 pp. 231-248.
Volinia S. et al. "A Human Phosphatidylinositol 3-kinase Complex Related to the Yeast Vps34p-Vps15p Protein Sorting System" (1995) EMBO Journal vol. 14, pp. 3339-3348.
Vivanco I. et al, "The Phosphatidylinositol 3-Kinase-AKT Pathway in Human Cancer" ( 2002) Nature Reviews Cancer (2002) vol. 2, pp. 489-550.
Shi Y. et al "Mammalian Target of Rapamycin Inhibitors Activate the AKT Kinase in Multiple Myeloma Cells by Up-Regulating the Insulin-like Growth Factor Receptor/Insulin Receptor Substrate-1/ Phosphatidylinositol 3-kinase Cascade" (2005) Mol Cancer Ther (2005) p. 1533.
Myohanen TT et al, A prolyl oligopeptidase inhibitor, KYP-2047, reduces [alpha]-synuclein protein levels and aggregates in cellular and animal models of Parkinson's disease, British Journal of Pharmacology; vol. 166, No. 3, Jun. 8, 2012, pp. 1097-1113.
Sakaguchi et al., "Prolyl oligopeptidase participates in cell cycle progression in a human neuroblastoma cell line", Biochemical and Biophysical Research Communications, vol. 409, No. 4, Jun. 1, 2011, pp. 693-698.
Duan L. et al., The Prolyl Peptidases PRCP/PREP Regulate IRS-1 Stability Critical for Rapamycin-induced Feedback Activation of P13K and AKT, The Journal of Biological Chemistry, vol. 289, No. 31, Aug. 1, 2014, pp. 21694-21705.

* cited by examiner

Figure 2A.
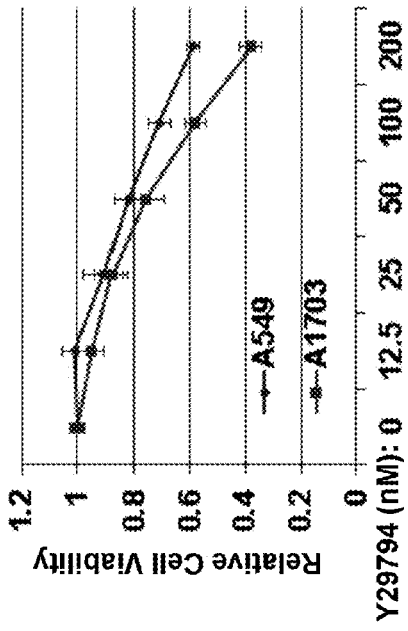
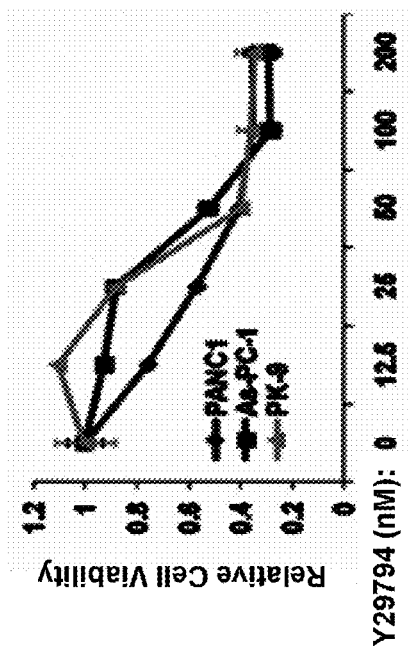
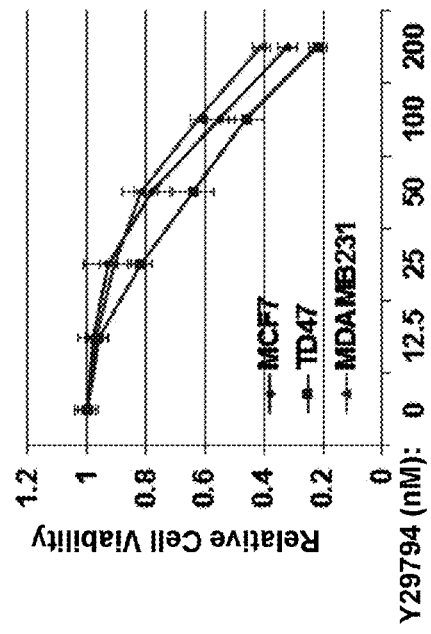

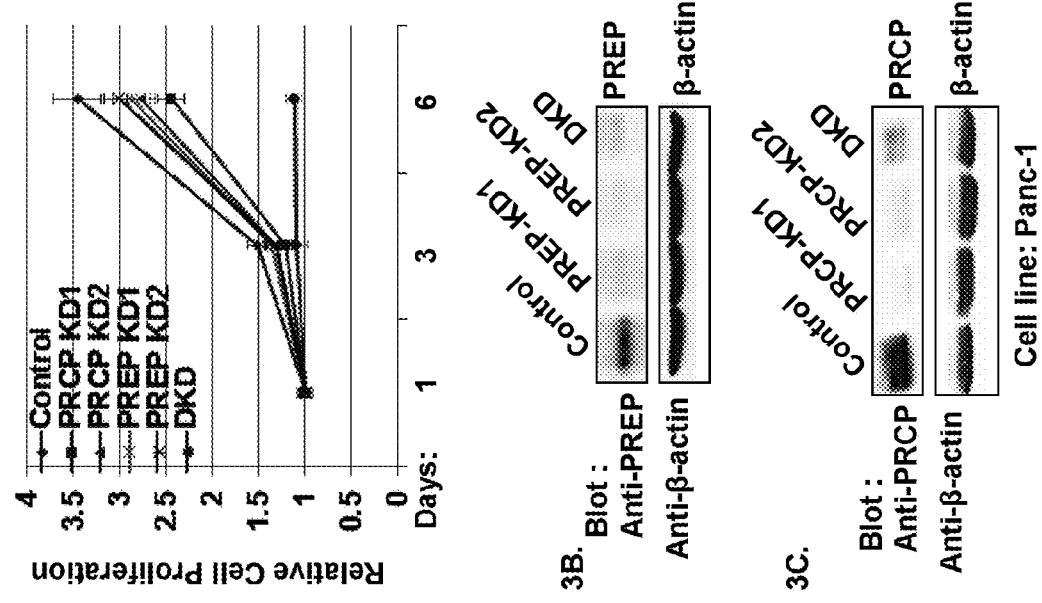

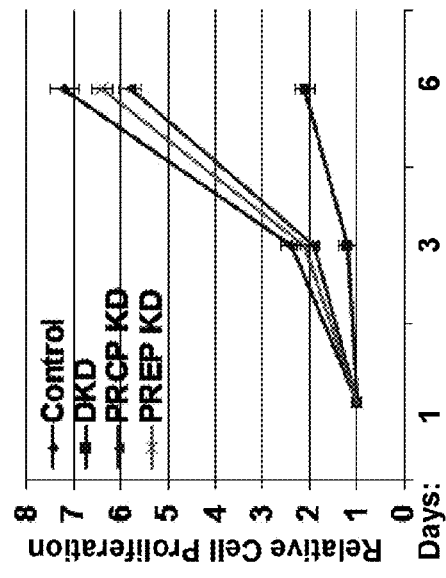
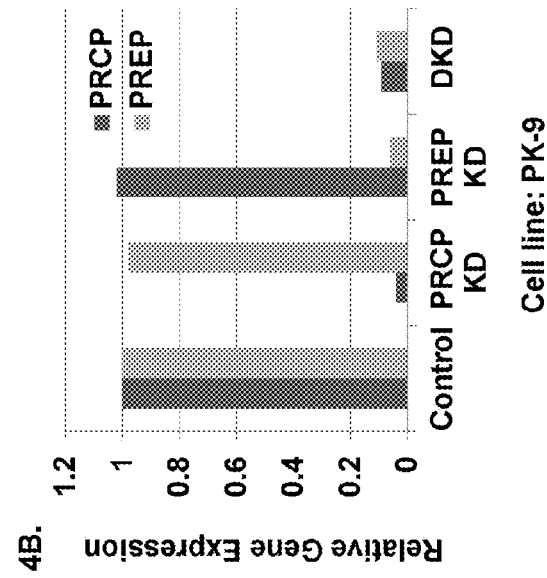
Figure 4A.
4B.

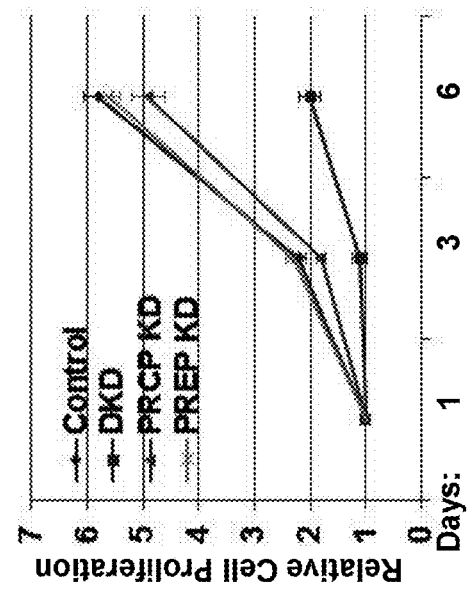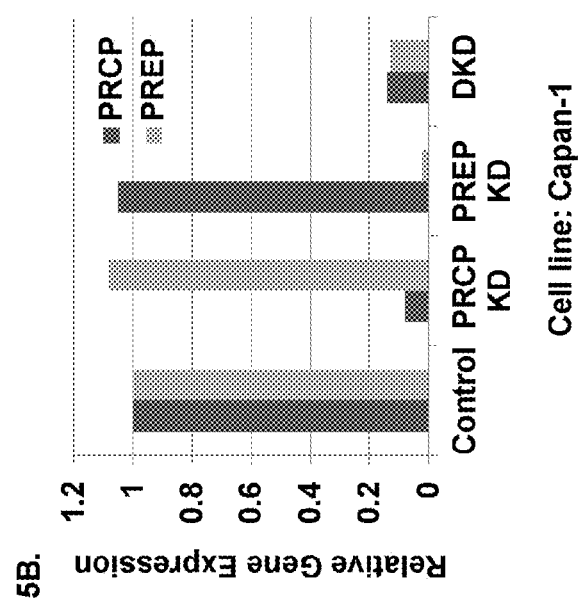
Figure 5A.
Figure 5B.

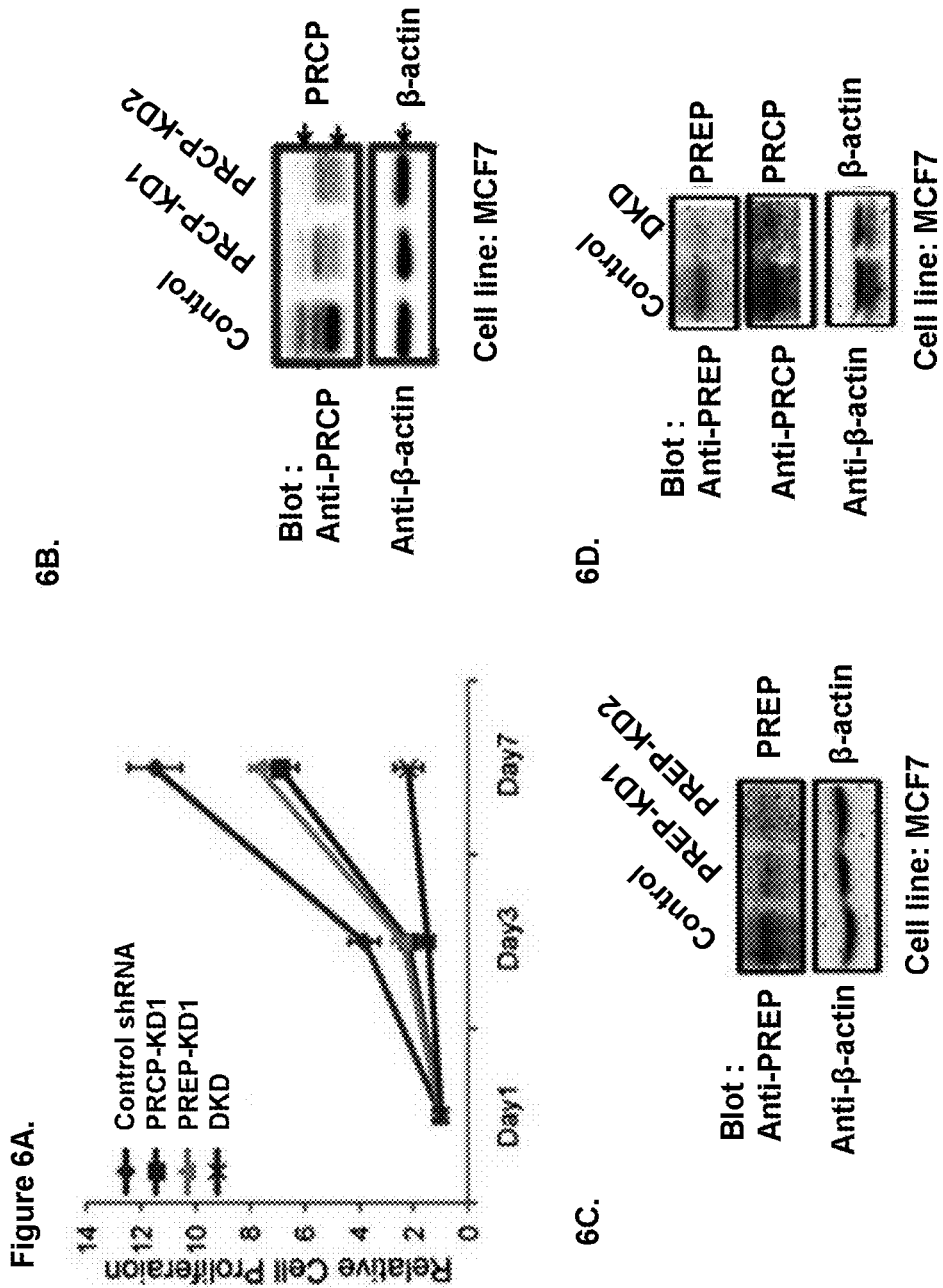

Figure 7A.
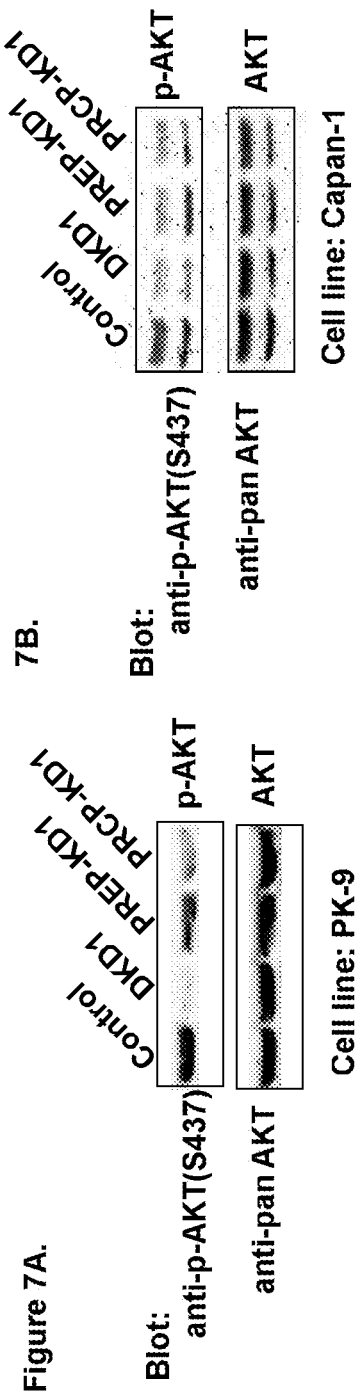
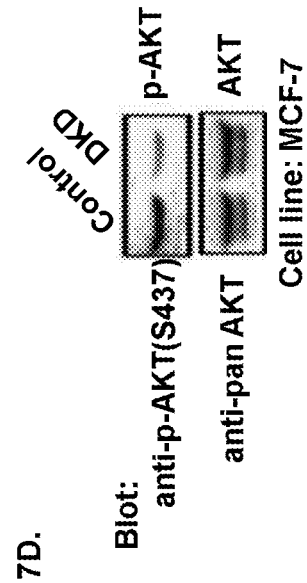
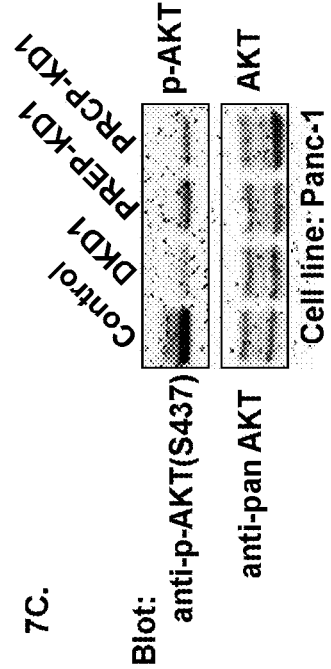

Figure 10A.
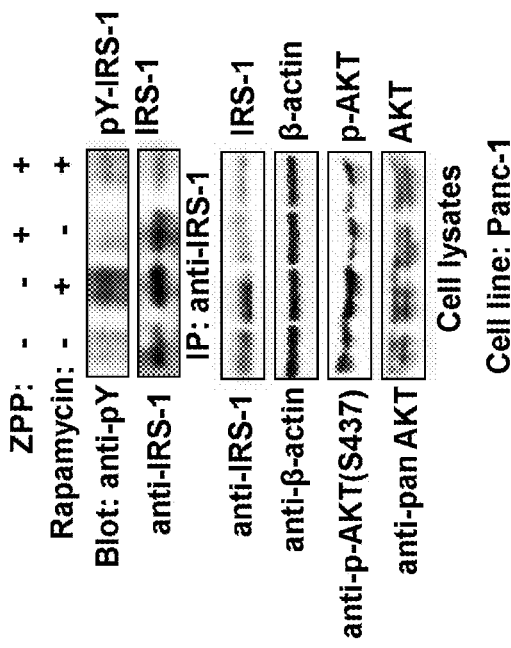
10B.
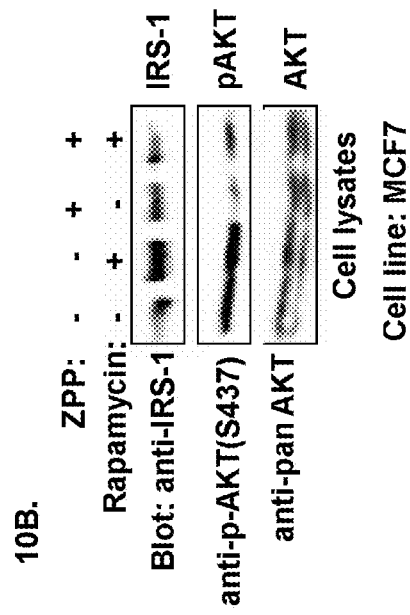

Figure 11A.
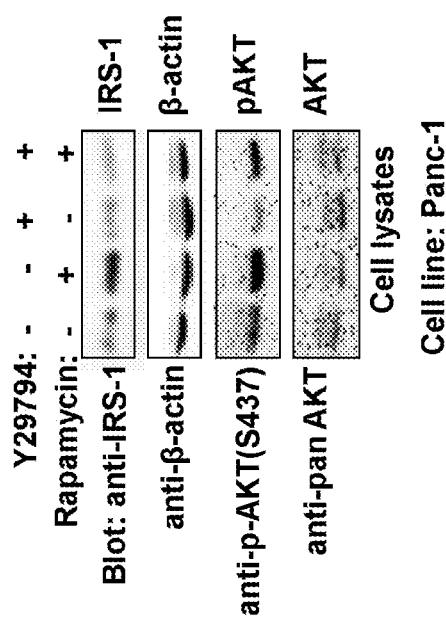
11B.
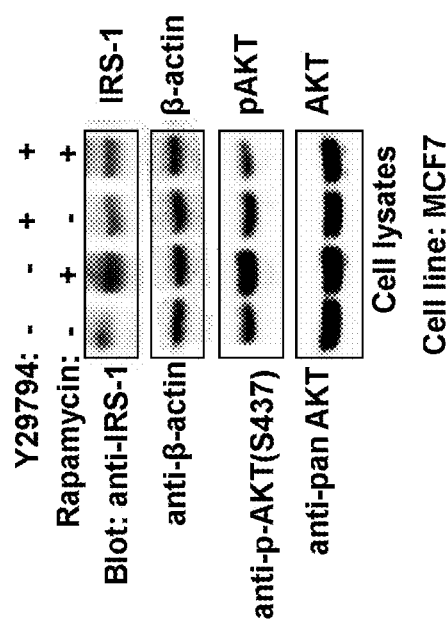

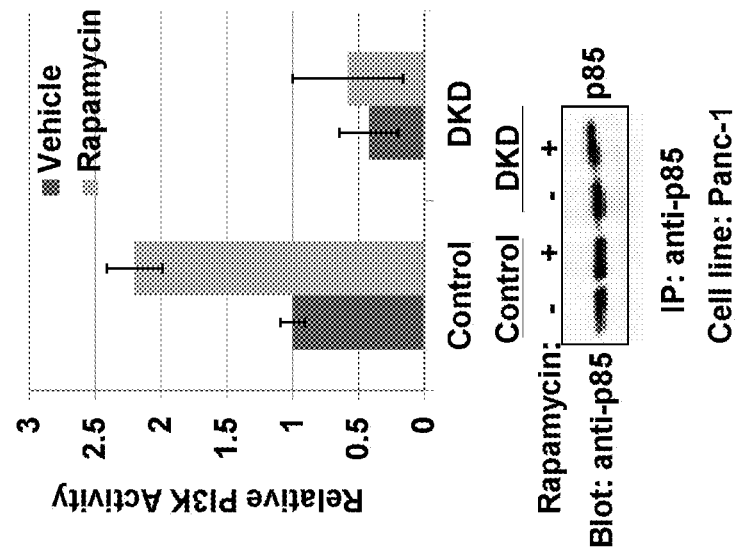
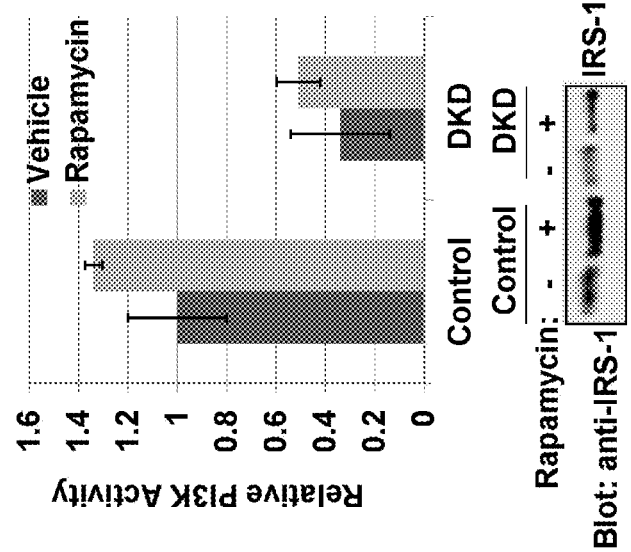
Figure 14A.

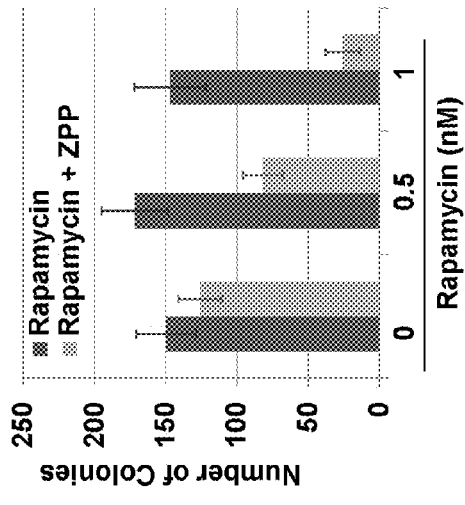
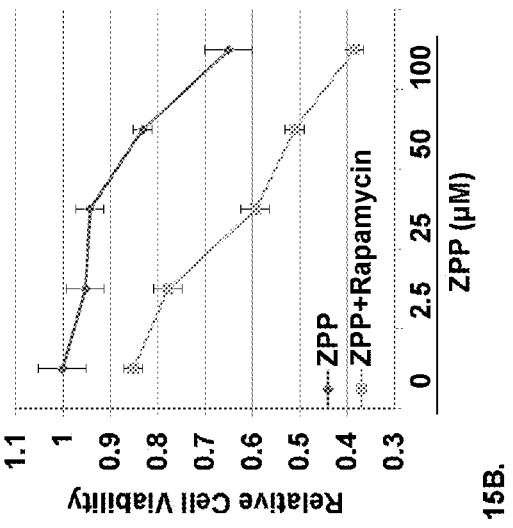
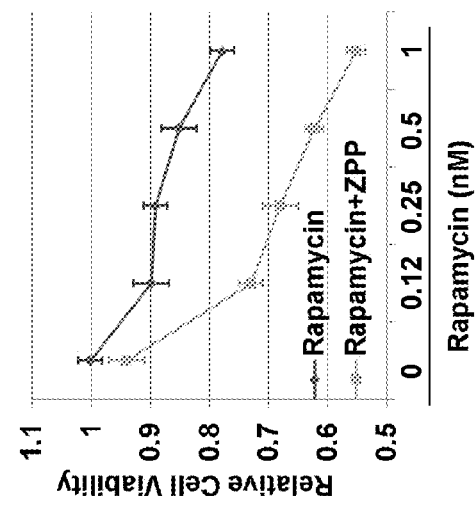
Figure 15A.
15B.
15C.

Figure 16A.
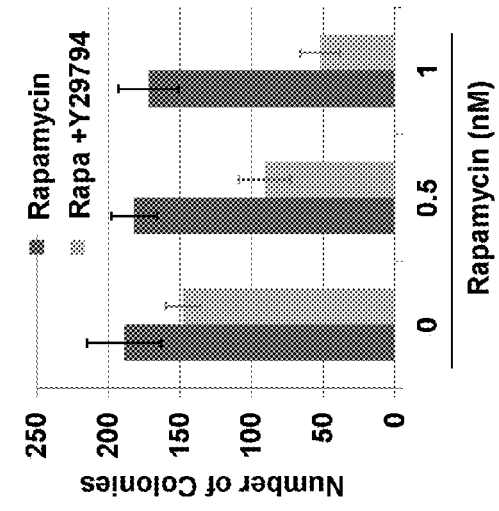
16B.
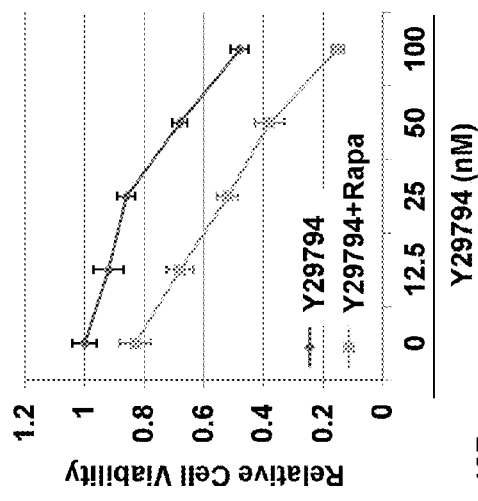
16C.
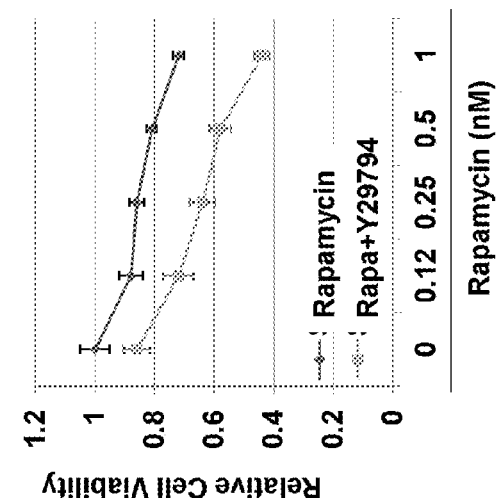

Figure 18A.
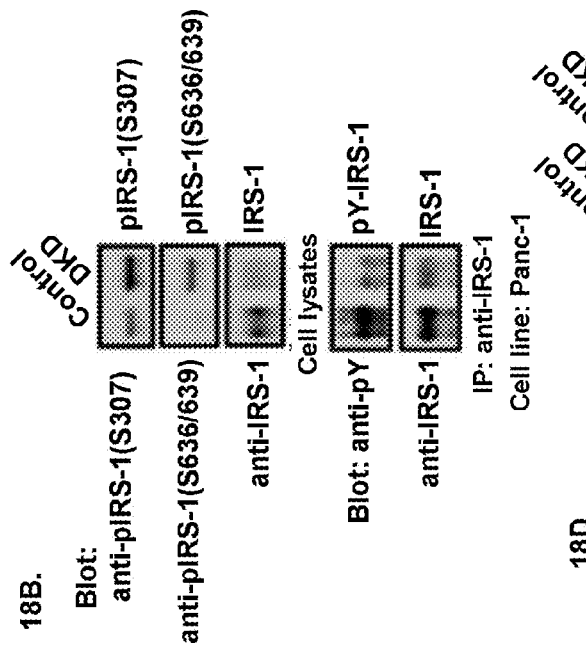
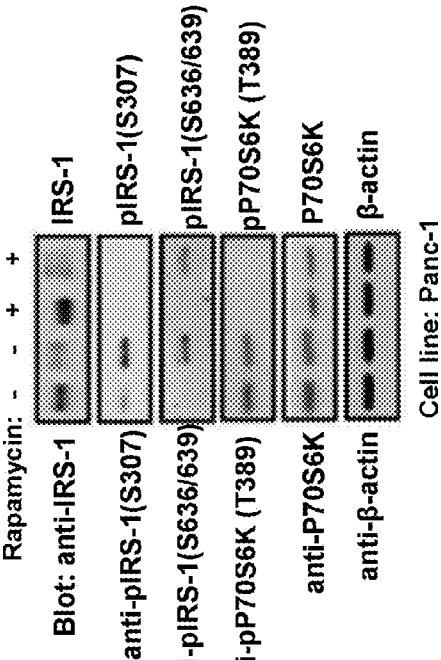
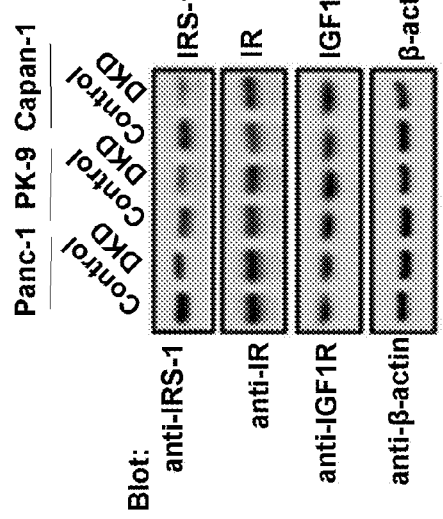
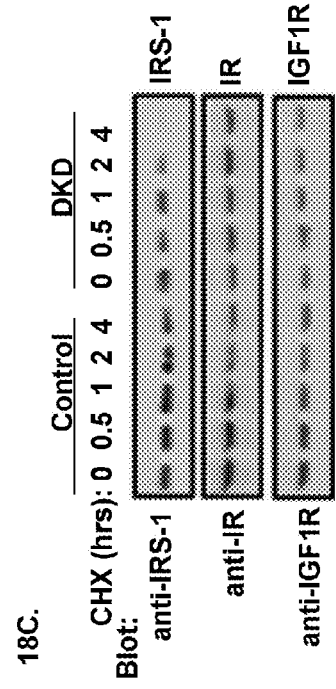

Figure 19A.
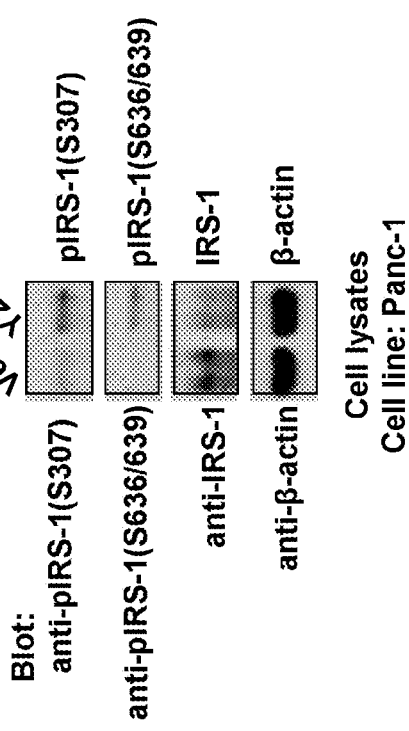
19B.
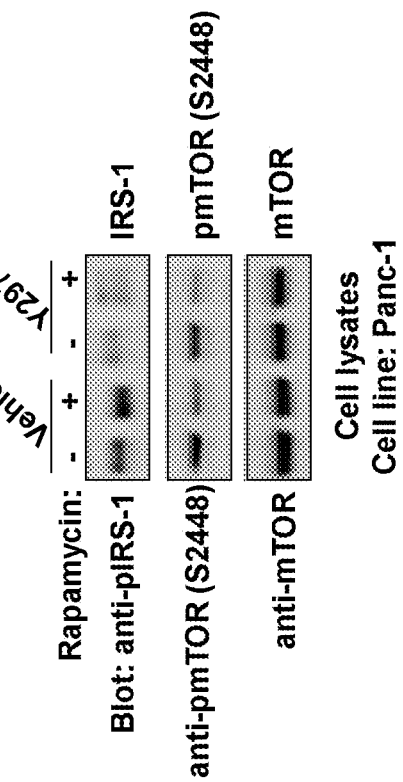

METHOD AND PHARMACEUTICAL COMPOSITION FOR INHIBITING PI3K/AKT/MTOR SIGNALING PATHWAY

CROSS-REFERENCE TO RELATED APPLICATIONS

This application is a national stage application of PCT/CN2013/001182 filed Sep. 29, 2013 which claims the benefit of priority to Chinese patent Application No. 20,210,379, 418.9.

TECHNICAL FIELD

Drug combinations and methods for inhibiting insulin receptor substrate and PI3K/AKT/mTOR signaling pathways are provided. The present invention relates to inhibition of a PI3K (phosphatidylinositol kinase (Phosphoinositide 3-kinase)/AKT (protein kinase B)/mTOR (mammalian target of rapamycin) signaling pathway for treating or preventing a disease. More particularly, the invention relates PRCP (prolylcarboxypeptidase) antagonist (i.e. anti-PRCP agent), or PREP (prolyl endopeptidase) antagonist anti-PREP agent), or a pharmaceutical composition of PREP/PRCP dual antagonist, a pharmaceutical composition comprising PREP antagonist or PRCP antagonist drugs and mTOR antagonists, or a pharmaceutical composition comprising PRCP and PREP dual antagonists and mTOR antagonist. The present invention also relates to the aforementioned pharmaceutical composition for treating or preventing diseases associated with activated PI3K/AKT/mTOR signaling pathway. Furthermore, the present invention also relates to the molecular mechanisms of stability and degradation of the insulin receptor substrate proteins and the use of PRCP antagonists, PREP antagonists, dual antagonists of PREP and PRCP for degradation of insulin receptor substrate proteins for treatment.

BACKGROUND

PRCP and PREP belong to prolyl peptidase family. Phylogenetic analysis shows that PRCP and PREP contain highly similar amino acid sequences, and have a similar enzyme function. They can cleave proline-containing substrates such as neuropeptide angiotensin II/III (AngII/III) and α-melanocyte stimulating hormone (α-MSH). PREP additionally cleaves nerve vasopressin (neurotensin) and gastrin-releasing hormone and other neuropeptides. These neuropeptides can activate G protein-coupled receptors (GPCR) and regulate the function of the receptor tyrosine kinase signaling pathway through the G protein-coupled receptors (Garcia-Horsman et al, (2007) Neutopeptides 41: 1-24; Rosenblum J S et al "(2003) Current Opinion in Chemical Biology, 7:496-504; Skidgel et al, (1998) Immunological Reviews, 161: 129-41. Rozengurt E et al, (2010) Clin Cancer Res; 16: 2505-11). Current research indicates that PRCP plays a role in obesity (Shariat-Madar B et al, (2010) Diabetes Metab Syndr Obes, 3: 67-78). Our previous study teaches that PRCP regulates breast cancer cell proliferation, autophagy, and resistance to the drug tamoxifen (Duan L et al, (2011) JBC, 286:2864-2876). PREP is also associated with amnesia, depression and Alzheimer's disease (Rosenblum J S et al, (2003) Current Opinion in Chemical Biology 7:496-504). Cell growth and proliferation are regulated by a number of different factors, including the availability of nutrients, growth factors (such as insulin and insulin-like growth factor, etc.) as well as the availability of the energy state of the cell, etc. PI3K/AKT/mTOR provide signal pathway integration of these factors to control cell growth and proliferation (Manning et al, (2007) Cell 129: 1261-1274; Engelman et al, (2006) Nat Rev Genet 7:606-619). Aberrant activation of PI3K/AKT/mTOR signaling pathway is considered to be the most common feature of all cancers (Engelman, J A, (2009) Nature Reviews/Cancer 9:550-562).

PI3K/AKT/mTOR signaling pathway is activated by RTKs (receptor tyrosine kinases), including the insulin receptor (IR), insulin-like growth factor receptor (IGF-1R), platelet-derived growth factor receptor (PDGFR) and epidermal growth factor receptor (EGFR).

RTKs can activate PI3K directly or indirectly through insulin receptor substrate (IRS) that interacts with PI3K p85 subunit and further activates PI3K p110 catalytic subunits (Markman et al., (2009) Ann Oncol. 21 (4): 683-91).

PI3K is an intracellular phosphatidylinositol kinase. There are three types of PI3K. Class I PI3Ks are mostly cytosolic, are heterodimers comprised of a p110 catalytic subunit and an adaptor/regulatory subunit, and are further divided into two subclasses: Class IA PI3Ks consist of a p110 catalytic subunit that associates with an SH2 domain-containing subunit p85, and is activated by the majority of tyrosine kinase-coupled transmembrane receptors; class IB PI3K consists of a p101 regulatory subunit that associates with p110γ catalytic subunit, and is activated by heterotrimeric GPCR. (Katso et al. (2001) Annu. Rev. Cell Dev. Biol. 17:615). Class II PI3Ks consist of three isoforms, as discussed herein. Class III PI3Ks utilize only phosphatidylinositol as a substrate, and play an essential role in protein trafficking through the lysosome. (Volinia, et al. (1995) EMBO J. 14:3339).

Class IA PI3K activity is suppressed in cytosol by p85 regulatory subunits that form heterodimers with the p110 catalytic subunit. IRS proteins (including IRS-1, IRS-1, IRS-3, IRS-4) are insulin receptor (IR) and insulin-like growth factor receptor (IGF-1R) adapter proteins. IR/IGF1R activates PI3K by regulating IRS protein tyrosine phosphorylation and subsequent interaction with PI3K p85 subunit. Many cancer tissues overexpress insulin receptor substrate IRS-1, while transgenic overexpression of IRS-1 or IRS-2 in mice caused breast cancer tumorigenesis and metastasis (Metz, et al, (2011) Clin Cancer Res 17: 206-211; Bergmann et al, (1996) Biochem Biophys Res Commun 220: 886-890; Dearth et al, (2006) Mol Cell Biol 26: 9302-9314). Tyrosine phosphorylation of IRS proteins is regulated by IR/IGF-1R and other RTKs such as EGFR and ErbB3 which activate IRS proteins. IRS proteins are also regulated by a number of serine/threonine kinases (for example. PKC, mTOR, S6K and ERK) that phosphorylate IRS proteins on serine leading to protein degradation and inhibition of IRS proteins (Copps et al (2012). Diabetologia. 55(10): 2565-2582). Degradation of insulin receptor substrates by certain drugs results in cell death in melanoma (Reuveni et al (2013) Cancer Res 73: 4383-4394). IRS proteins phosphorylated on tyrosine interact with the SH2 domain of p85 subunit resulting in recruitment of PI3K to membrane and release of the inhibitory effect of p85 leading to activation of PI3K. PI3Ks are enzymes that phosphorylate the 3-hydroxyl position of the inositol ring of phosphoinositides ("PIs"). Activated PI3K generates phosphatidylinositol 3-phosphate (PI3P) that serves as a secondary messenger in growth signaling pathways, influencing cellular events including cell survival, migration, motility, and proliferation; oncogenic transformation; tissue neovascularization; and intracellular protein trafficking. PI3P activates the PI3K-dependent protein kinase-1 (PDK1), which in turn activates the kinase AKT. AKT phosphorylates downstream target molecules to promote cell proliferation, survival and neovascularization. (Cantley et al. (1999) PNAS 96:4240) mTOR is an important signaling molecule downstream of the PI3K/AKT pathway (Grunwald et al. (2002) Cancer Res. 62: 6141; Stolovich et al. (2002) Mol Cell Biol. 22: 8101). AKT-mediated phosphorylation inhibits the GAP activity of TSC1/TSC2 toward the Rheb GTPase, leading to Rheb activation. Rheb binds directly to mTOR, a process that is regulated by amino acids. Both amino acids and Rheb activation are required for mTOR activation. mTOR downstream effector molecules include p70 S6 ribosomal protein kinase (S6K) and eukaryotic initiation factor binding inhibitory protein (4E-BP1). After the activation mTOR phosphorylates and activates the catalytic activity S6K1. mTOR also catalyzes phosphorylation of 4E-BP1 and inactivates it, resulting in initiation of protein translation and cell cycle progression (Kozma et al, (2002) Bioessays 24: 65). More importantly, mTOR exerts a negative feedback on activation of PI3K/AKT by suppressing expression and activation of IRS proteins. Inhibition of mTOR by rapamycin relieves the negative inhibition leading to activation of PI3K AKT (Shi et al (2005) Mol Cancer Ther 2005; 4(10): 1533).

PI3K/AKT/mTOR signaling pathway inhibition is considered a promising cancer treatment (Engelman, J A, (2009) Nature Reviews: Cancer 9:551). mTOR antagonist rapamycin is the first signaling target in the PI3K/AKT/mTOR pathway for anti-cancer treatment (Courtney et al, (2010) J Clin Oncol 28: 1075-1083; Vivanco et al, (2002) Nat Rev Cancer 2:489-50). Unfortunately, rapamycin lifts the negative feedback inhibition of IRS proteins, leading to the activation of PI3K and AKT. Patients treated by rapamycin show increased AKT phosphorylation in tumors, leading to failure of tumor treatment (Easton et al, (2006) Cancer Cell. 9 (3):153-5) Therefore, there is a need to develop means to effectively inhibit the PI3K/AKT/mTOR signaling pathway, in particular to prevent the feedback activation of IRS proteins upon inhibition of mTOR.

SUMMARY OF THE INVENTION

The present invention relates to pharmaceutical agents that can inhibit PI3K/AKT and prevent mTOR antagonists (for example, rapamycin) induced feedback activation of PI3K and AKT, and such agents alone or in combination with mTOR antagonists will be used to treat PI3K/AKT/mTOR related diseases. Accordingly, the present invention also relates to the method and use of the pharmaceutical composition for the treatment and prevention of PI3K/AKT/mTOR-related diseases, in one aspect, the present invention includes introducing to patient an effective amount of PRCP antagonist, PREP antagonist, or an effective amount of PRCP and PREP dual antagonist for inhibition of PI3K/AKT/mTOR signaling pathway, thereby treating or preventing cancer and diseases caused by abnormal activation of PI3K/AKT/mTOR signaling pathway. Antagonists include, but are not limited to the use of chemical inhibitors or inhibitory nucleotides. In another aspect, the invention also uses PRCP antagonists, PREP antagonists or dual antagonist PREP and PRCP to prevent feedback activation of PI3K/AKT by mTOR antagonists.

A. To use the effective dose by combining PRCP antagonists and mTOR antagonists, or joint use of effective dose PREP antagonists and mTOR antagonists, or a combination of the effective dose of PRCP PREP dual antagonists and mTOR antagonists to inhibit PI3K/AKT/mTOR signaling pathway, thereby treating or preventing abnormal activation of the PI3K/AKT/mTOR pathway related diseases. Antagonists include, but are not limited to the use of chemical inhibitors or inhibitory nucleotides. Furthermore, the present invention also relates to the use of PRCP antagonists, PREP antagonists or dual antagonist PREP PRCP to destroy IRS proteins by using an effective amount of an antagonist for the aforementioned degradation of IRS protein, thereby treating or preventing diseases related to IRS proteins, including the PI3K/AKT/mTOR activation related diseases, especially cancer. The aforementioned invention, PRCP antagonist, PREP antagonists, or PREP and PRCP antagonists can be any dual antagonist. For example, they may be inhibitory nucleotides. Preferably, PRCP PREP antagonists and small molecule antagonists, and derivatives thereof; More preferably, the small-molecule compound is (tert-butyl (2s)-2-{[(2s)-2-formylpyrrolidin-1-yl] carbonyl}pyrrolidine-1-carboxylate) (Z-Pro-Prolinal or ZPP) and derivatives, and small molecule compounds [2-[8-(dimethylamino)octylsulfanyl]-6-propan-2-ylpyridin-3-yl]-thiophen-2-ylmethanone (Y29794) and derivatives thereof. Further, preferably the small molecule antagonists of mTOR are rapamycin and derivatives thereof. Wherein, preferably PI3K/AKT/mTOR abnormal activation of the signal pathway associated disease is cancer, neurodegenerative diseases, metabolic diseases, hamartoma syndrome and hereditary myopathy.

BRIEF DESCRIPTION OF THE DRAWINGS

FIGS. 1A-1D. ZPP ((tert-butyl(2s)-2-{[(2s)-2-formylpyrrolidin-1-yl]carbonyl}pyrrolidine-1-carboxylate)) induces cytotoxicity in cancer cells analyzed by MTT assay and colony formation assay (clonogenesis assay). FIG. 1A reports relative cell viability for cell lines Panc-1, AsPC-1, PK-9 and Capan-1 treated with ZPP at various concentrations. FIG. 1B reports relative cell viability for cell lines A549 and A1703 treated with various concentrations of ZPP. FIG. 1C reports relative cell viability for cell lines T47D and MCF7. FIG. 1D is a colony forming analysis for Panc-1 cell line treated with various concentrations of ZPP.

FIG. 2A-2C. Y29794 ([2-[8-(dimethylamino)octylsulfanyl]-6-propan-2-ylpyridin-3-yl]-thiophen-2-ylmethanone) induces cytotoxicity in cancer cells analyzed by MTT assay. FIG. 2A reports relative cell viability for cell lines Panc-1 AsPC-1, and PK-9 cells treated with various concentrations of Y29794. FIG. 2B reports relative cell viability for cell lines A549 and A1703 treated with various concentrations of Y29794. FIG. 2C reports relative cell viability for cell lines MDAMB231, T47D and MCF7 treated with various concentrations of Y29794.

FIG. 3. Gene silencing of PRCP or PREP individually by lentiviral shRNA reduces proliferation while gene silencing of both PRCP and PREP blocks cell proliferation in Panc-1 pancreatic cancer cells. FIG. 3A reports reduced proliferation of Panc-1 cells with knockdown of PRCP and/or PREP compared with control cells. FIG. 3B reports reduction of PREP protein in the cells with knockdown of PREP. FIG. 3C reports reduction of PREP protein in the cells with knockdown of PRCP. KD1, KD2—knockdown 1 or 2 of corresponding genes; DKD—double knockdown of PRCP and PREP.

FIG. 4. Gene silencing of PRCP or PREP individually by lentiviral shRNA reduces proliferation while gene silencing of both PRCP and PREP blocks cell proliferation in PK-9 pancreatic cancer cells. FIG. 4A reports reduced proliferation of PK-9 cells with knockdown of PRCP and/or PREP compared with control cells. FIG. 4B reports reduction of PRCP and/or PREP mRNA in the cells with knockdown of PRCP and/or PREP, KD—knockdown of corresponding genes; DKD—double knockdown of PRCP and PREP.

FIG. 5. Gene silencing of PRCP or PREP individually by lentiviral shRNA reduces proliferation while gene silencing of both PRCP and PREP blocks cell proliferation in Capan-1 pancreatic cancer cells. FIG. 5A reports reduced proliferation of Capan-1 cells with knockdown of PRCP and/or PREP compared with control cells. FIG. 5B reports reduction of PRCP and/or PREP mRNA in the cells with knockdown of PRCP and/or PREP. KD—knockdown of corresponding genes; DKD—double knockdown of PRCP and PREP.

FIG. 6. Gene silencing of PRCP or PREP individually by lentiviral shRNA reduces proliferation while gene silencing of both PRCP and PREP blocks cell proliferation in MCF7 breast cancer cells. FIG. 6A reports reduced proliferation of MCF7 cells with knockdown of PRCP and/or PREP. FIG. 6B reports reduction of PRCP protein in the cells with knockdown of PRCP. FIG. 6C reports reduction of PREP protein in the cells with knockdown of PREP. FIG. 6D reports reduction of PRCP and PREP protein in the cells with knockdown of PRCP and PREP. KD1, KD2—knockdown of corresponding genes with two different pairs of shRNA (#1 or #2); DKD—double knockdown of PRCP and PREP.

FIG. 7 AKT phosphorylation is inhibited by gene silencing of PRCP and/or PREP in Panc-1, PK-9, Capan-1 and MCF7 cells by immunoblot analysis. FIG. 7A reports reduced AKT phosphorylation (S473) in Panc-1 cells with knockdown of PRCP and/or PREP. FIG. 7B reports reduced AKT phosphorylation (S473) in Capan-1 cells with knockdown of PRCP and/or PREP. FIG. 7B reports reduced AKT phosphorylation (S473) in Panc-1 cells with knockdown of PRCP and/or PREP. FIG. 7D reports reduced AKT phosphorylation (S473) in MCF7 cells with knockdown of PRCP and PREP. KD1, KD2—knockdown of corresponding genes with shRNA #1; DKD—double knockdown of PRCP and PREP.

FIG. 8. AKT phosphorylation is inhibited by ZPP or Y29794 in Panc-1, PK-9, and MCF7 cells by immunoblot analysis. FIG. 8B reports reduced AKT phosphorylation (S473) in MCF7 cells treated with ZPP (400 µM) compared with cells treated with vehicle (DMSO). FIG. 8C reports reduced AKT phosphorylation (S473) in Panc-1 cells treated with ZPP (400 µM) compared with cells treated with vehicle (DMSO). FIG. 8D reports reduced AKT phosphorylation (S473) in Panc-1 cells treated with Y29794 (1 µM) compared with cells treated with vehicle (Ethanol). FIG. 8E reports reduced AKT phosphorylation (S473) in MCF7 cells treated with Y29794 (1 µM) compared with cells treated with vehicle (Ethanol). FIG. 8F reports reduced AKT phosphorylation (S473) in PK-9 cells treated with Y29794 (1 µM) compared with cells treated with vehicle (Ethanol).

FIG. 9 also reports that increase in rapamycin-induced feedback in IRS-1 expression and AKT phosphorylation is inhibited by gene silencing of PRCP and PREP in Panc-1 cells. KD—knockdown of corresponding genes with shRNA #1; DKD—double knockdown of PRCP and PREP.

FIG. 10. ZPP reduces rapamycin-induced feedback increase in IRS-1 and AKT phosphorylation in Panc-1 and MCF cells by immunoblot analysis. FIG. 10A reports that Panc-1 cells treated with rapamycin (10 nM) have increased IRS-1 protein, tyrosine phosphorylation of IRS-1, and phosphorylated AKT (S473), and that Panc-1 cells treated with ZPP (400 µM) have reduced IRS-1 proteins and phosphorylated AKT (S473), while in cells treated with ZPP and rapamycin, ZPP blocks rapamycin-induced increase in IRS-1 protein and phosphorylated AKT (S473). FIG. 10B reports that MCF7 cells treated with rapamycin (10 nM) have increased IRS-1 protein and phosphorylated AKT (S473) and that MCF7 cells treated with ZPP (400 µM) have reduced IRS-1 proteins and phosphorylated AKT (S473), while in cells treated with ZPP and rapamycin, ZPP blocks rapamycin induced increase in IRS-1 protein and phosphorylated AKT (S473).

FIG. 11. Y29794 reduces rapamycin-induced feedback increase in IRS-1 and AKT phosphorylation in Panc-1 and MCF cells by immunoblot analysis. FIG. 11A reports that Panc-1 cells treated with rapamycin (10 nM) have increased IRS-1 protein and phosphorylated AKT (S473) and that Panc-1 cells treated with Y29794 (0.5 µM) have reduced phosphorylated AKT (S473), while the cells treated with Y29794 and rapamycin, Y29794 blocks rapamycin induced increase in IRS-1 protein and phosphorylated AKT (S473). FIG. 11B reports that MCF7 cells treated with rapamycin (10 nM) have increased IRS-1 protein and phosphorylated AKT (S473), while in cells treated with Y29794 and rapamycin, Y29794 blocks rapamycin induced increase in IRS-1 protein and phosphorylated AKT (S473).

FIG. 12 reports that Panc-1 cells treated with rapamycin have increased PI3K activity compared with vehicle-(DMSO)-treated cells by PI3K kinase assay in anti-p85 immunoprecipitates. FIG. 12 also reports that Panc-1 cells treated with ZPP or Y29794 have reduced PI3K activity, and that ZPP or Y29794 also blocks rapamycin-induced feedback increase in PI3K activity.

FIG. 13 reports that Panc-1 cells treated with ZPP (400 µM) or Y29794 (0.5 µM) have reduce PI3K activity compared with vehicle (DMSO)-treated cells by PI3K kinase assay of anti-IRS-1 immunoprecipitates. FIG. 13 also reports that ZPP or Y29794 also reduces tyrosine phosphorylation of IRS-1 and coimmunoprecipitation of p85 with IRS-1.

FIG. 14. Gene silencing of PRCP and PREP reduces PI3K activity and blocks rapamycin-induced feedback increase in PI3K activity. FIG. 14A reports that in Panc-1 cells rapamycin increases IRS-1 protein and IRS-1 associated PI3K activity, and that in Panc-1 cells with double knockdown of PRCP and PREP, both IRS-1 protein and IRS-1 associated PI3K activity are reduced, and that this reduction is not reversed by rapamycin as shown by PI3K kinase assay in anti-IRS-1 immunoprecipitates (IP). FIG. 14B reports that in Panc-1 cells rapamycin increases p85-associated PI3K activity, and that in Panc-1 cells with double knockdown of PRCP and PREP p85-associated PI3K activity is reduced, and that this reduction is not reversed by rapamycin as shown by PI3K kinase assay in p85 IP. DKD—double knockdown of PRCP and PREP.

FIG. 15. Combination of ZPP and rapamycin induces synergistic cytotoxicity by MTT assay and colony formation assay in Panc-1 cells. FIG. 15A reports that Panc-1 cells treated with various concentration of ZPP in combination with 0.5 nM of rapamycin for three days have synergistic reduction in cell viability. FIG. 15B reports that Panc-1 cells treated with various concentration of rapamycin in combination with 25 µM of ZPP for three days have synergistic reduction in cell viability. FIG. 15C reports that Panc-1 cells treated with various concentration of rapamycin in combination with 50 µM of ZPP for 7 days have synergistic reduction in cell colonies formed at 21 days.

FIG. 16. Combination of Y29794 and rapamycin induces synergistic cytotoxicity by MTT assay and colony formation assay in Panc-1 cells. FIG. 16A reports that Panc-1 cells treated with various concentration of Y29794 in combination with 0.5 nM of rapamycin for three days have synergistic reduction in cell viability. FIG. 16B reports that Panc-1 cells treated with various concentration of rapamycin in combination with 25 nM of Y29794 for three days have synergistic reduction in cell viability. FIG. 16C reports that Panc-1 cells treated with various concentration of rapamycin in combination with 25 nM of Y29794 for 7 days have synergistic reduction in cell colonies formed at 21 days.

FIG. 17 reports that treatment of SCID mice with xenotransplanted Panc-1 tumor cells by Y29794 significantly reduces Panc-1 tumor growth; FIG. 17 also reports that treatment with combination of rapamycin and Y29794 has synergistic effect in inhibition of Panc-1 tumor growth.

FIG. 18. Gene silencing of PRCP and PREP induces serine phosphorylation and degradation of IRS-1 by immunoblot analysis. FIG. 18A reports that in Panc-1, PK-9 and Capan-1 cells knockdown of PRCP and PREP reduces IRS-1 protein. FIG. 18B reports that in Panc-1 cells knockdown of PRCP and PREP induces serine phosphorylation (S307 and S636/639) of IRS-1 while reduces tyrosine phosphorylation of IRS-1. FIG. 18C reports that in Panc-1 cells knockdown of PRCP and PREP decreases IRS-1 half-life when protein synthesis is blocked by cycloheximide (CHX, 20 µg/ml). FIG. 18D reports that in control Panc-1 cells rapamycin inhibits serine phosphorylation (S307 and S636/639) and increases IRS-1 protein; while in Panc-1 cells with knockdown of PRCP and PREP rapamycin does not inhibit S636/639 phosphorylation and does not increase IRS-1 protein. DKD—double knockdown of PREP and PREP.

FIG. 19. Y29794 induces serine phosphorylation and degradation of IRS-1 and blocks rapamycin-induced feedback increase in IRS-1. FIG. 19A reports that in Panc-1. PK-9 and Capan-1 cells Y29794 (1 µM) reduces IRS-1 protein. FIG. 19B reports that in Panc-1 cells Y29794 (1 µM) induces serine phosphorylation (S307 and S636/639) of IRS-1 and reduces IRS-1 protein. FIG. 19C reports that in Panc-1 cells Y29794 (1 µM) decreases IRS-1 half-life in the presence of CHX. FIG. 19D reports that in Panc-1 cells rapamycin induces increased IRS-1 protein level and inhibits mTOR phosphorylation, while Y29794 (1 µM) inhibits repamycin-induced increase in IRS-1 protein without affecting mTOR phosphorylation.

DETAILED DESCRIPTION OF THE INVENTION

Figure 1A:
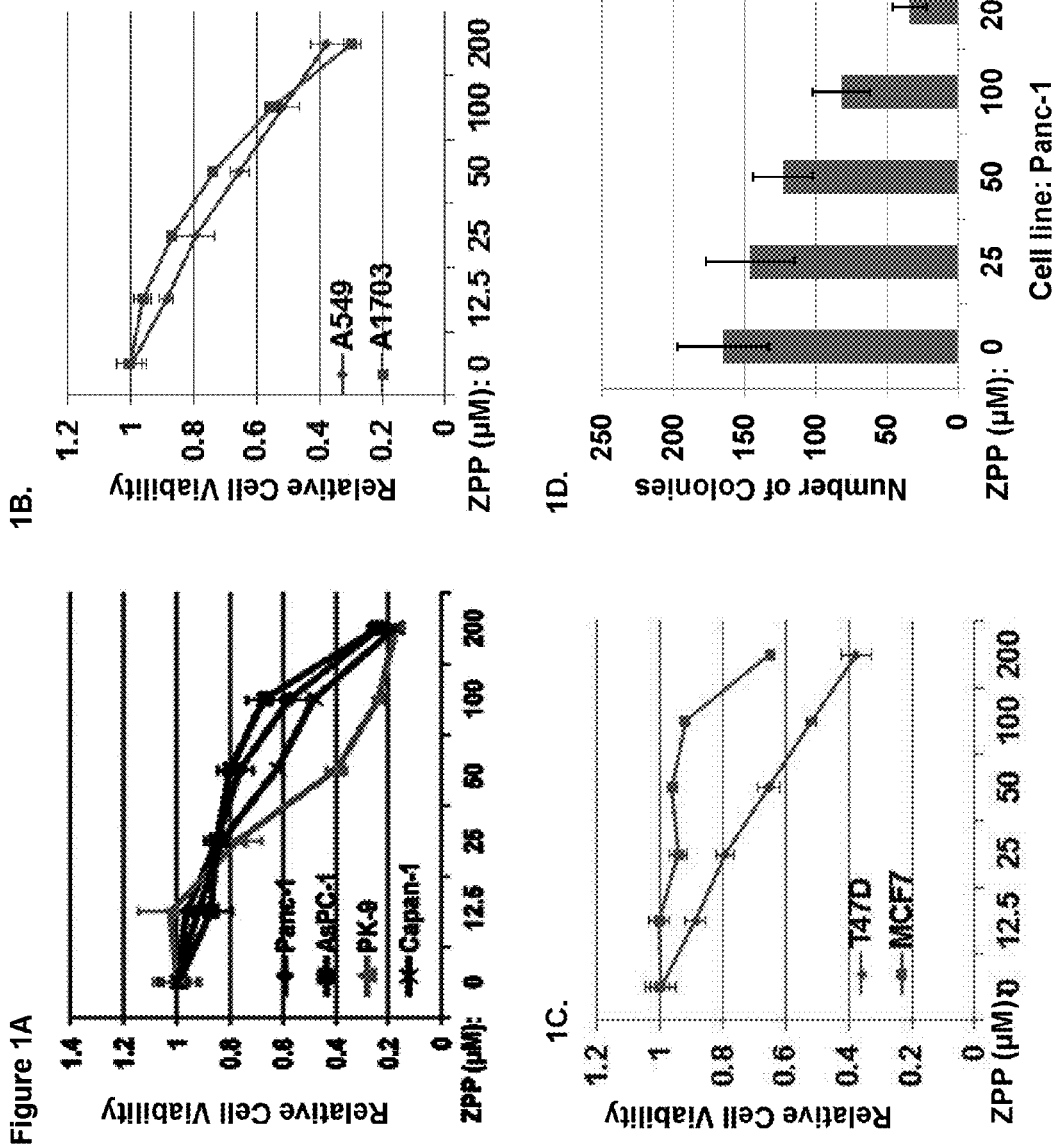

The present invention, PRCP (gene library designation number (accession number NP-005031, which isoforms (isoform) 1 is NP-005031.1; isoform 2 is NP-955450.2) refers to a part of prolyl peptidase family and the family of carboxypeptidase serine peptidase. PRCP human amino acid sequence is shown in SEQ ID No. 1. PRCP cleaves the C-terminal proline peptide bond in the peptide. The present invention, PREP (gene library specified number NP-002717) belongs to the prolyl peptidase family. PREP human amino acid sequence is shown in SEQ ID No. 2. Phylogenetic analysis shows that PRCP and PREP contain highly similar amino acid sequences, and have a similar enzyme function. PRCP and PPEP can cleave substrates such as neuropeptide angiotensin II/III (Ang ll/III) and α-melanocyte stimulating hormone (α-MSH). PREP additionally cleaves vasopressin (neurotensin) and gastrin-releasing hormone (gastrin-releasing hormone) and other neuropeptides. These neuropeptides activate G protein-coupled receptor (GPCR) and regulate receptor tyrosine kinase signaling pathway function through the G protein-coupled receptors (2007) Neutopeptides 41: 1-24; Rosenblum J S et al, (2003) Curr Opin Chem Biol., 7:496-504; Skidgel et al, (1998) Immunological Reviews, 161: 129-41). Prolyl peptidase family includes acylaminoacyl peptidase (AAP), dipeptidyl-peptidases (DPP4, DPP7, DPP8, DPP9, fibroblast activation protein alpha (FAP)) (Rosenblum J S et al, (2003) Current Opinion in Chemical Biology, 7:496-504). PRCP is associated with obesity (Shariat-Madar B et al, (2010) Diabetes Metab Syndr Obes, 3: 67-78). PRCP knockout mice was lower weight than the wild-type mice Inhibition of PRCP enzyme function can also reduce mouse body weight. Our own research found that PRCP regulates cell proliferation, autophagy and resistance to tamoxifen in breast cancer cells (Duan L et al, (2011) JBC, 286:2864-2876). DPP4 is associated with obesity and diabetes. DPP4 knockout mice fled with high-fat foods have lower body weight than wild-type mice and are more sensitive to insulin (Richter B et al, (2008) Cochrane Database Syst Rev, 16; (2): CD006739). DPP4 inhibitors are used to treat diabetes. DPP7 regulate the static lymphocyte survival. FAP overexpression increased cell proliferation. PREP is associated with amnesia, depression and Alzheimer's disease (Rosenblum J S et al, (2003) Current Opinion in Chemical Biology 7:496-504).

"Antagonist" used herein refers to the in vitro and in vivo agents that can reduce or prevent PRCP, PREP, and mTOR function. PRCP and PREP antagonists include but are not limited to, antagonists of other proteins with similar functions within the carboxypeptidase family and the prolyl peptidase family. mTOR antagonists include, but are not limited to antagonists for other proteins involved in the activation of the mTOR signaling pathway. As used herein, the term refers to the inhibitory polynucleotide capable of inhibiting the expression of genes. Typical inhibitory polynucleotides include but not limited to antisense oligonucleotides (Antisense oligonucleotides), triple helix DNA (triple helix DNA), RNA aptamers (aptamers), ribozymes (ribozymes), short inhibiting ribonucleotide (siRNA), short hairpin RNA (shRNA) and microRNA. For example, siRNA, microRNA, or antisense oligonucleotides designed based on the known sequence of PRCP and PREP to inhibit the expression of PRCP and PREP. Similarly, ribozymes can be synthesized to recognize specific nucleotide sequences of the gene and cut it. The skilled in the art person is fully capable of using such prior art designs for gene inhibition without further development.

"Small molecule compounds" used herein refers to compounds with a molecular weight of less than 3 kilodaltons. A compound can be organic or a natural product.

"Effective dose" used herein refers to the dose which will affect the biological function of the target molecule or signaling pathway, and thus can prevent or ameliorate clinical symptoms or condition. The effective dose is determined based on the intended goal. The effective dose also refers to a dose that can reduce at least 10% of a target molecule or pathway activity or function in the host, preferably reduce 30% or more preferably 50-90%.

"P13K/AKT/mTOR pathway-related diseases, P13K/AKT/mTOR signaling pathway abnormalities caused by disease. PI3K/AKT/mTOR signal abnormalities caused by disease, PI3K/AKT/mTOR signal-related diseases and disorders caused by signals of the same" used herein include, but are not limited to, cancer, organ transplant-related disorders (for example, reduce the rate of rejection, graft-versus-host disease, etc.), muscular sclerosis, arthritis, allergic encephalomyelitis, immunosuppression-related disorders, metabolic disorders (for example, obesity, diabetes, etc.), reducing intimal thickening after vascular injury, protein misfolding diseases (for example, Alzheimer's disease, Gaucher's disease, Parkinson's disease, Huntington's disease, cystic fibrosis, macular degeneration, retinitis pigmentosa, diabetic retinopathy, prion disease, etc.). PI3K/AKT/mTOR signaling pathway-related diseases include hamartoma syndromes, such as tuberous sclerosis and multiple hamartoma syndrome. Hamartoma is a general term for benign tumor-like malformation composed of mature cells and tissue normally found in the affected area that have grown in a disorganized manner.

PI3K/AKT/mTOR signaling pathway related disorders also include hereditary myopathy, myopathy such as myotubes. Myotubes myopathy is characterized by decrease in activity of muscle tubulin phosphatase (myotubularin). Myotubularin is a 3-phosphoinositide phosphatase.

"Cancer" is used herein to include mammalian solid tumors and hematologic malignancies, including but not limited to head and neck cancers lung cancer, pleural mesothelioma, esophageal cancer, gastric cancer, pancreatic cancer, hepatobiliary cancer, small bowel cancer, colon cancer, colorectal cancer, kidney cancer, urinary tract cancer, bladder cancer, prostate cancer, penile cancer, testicular cancer, gynecological cancer, ovarian cancer, breast cancer, endocrine system cancer, skin cancer, CNS cancer, soft tissue sarcoma, osteosarcoma and melanoma. Hematologic malignancies include but is not limited to lymphoma, multiple myeloma, Hodgkin's disease, leukemia, plasma cell tumors and AIDS-related cancer. In addition, all of the other cancers, including primary cancer, metastatic cancer, in the context of recurrent cancer. Preferably the present invention for treating or preventing cancer and PI3K/AKT/mTOR abnormal activation of signaling pathways related to cancer diseases, neurodegenerative diseases, metabolic diseases, hamartoma syndrome and hereditary myopathy. Preferably the present invention for treating or preventing cancer and abnormal activation of PI3K/AKT/mTOR signaling pathway related to breast cancer, pancreatic cancer or lung cancer.

The present invention provides treating or preventing abnormal activation of PI3K/AKT/mTOR signal pathway associated disorders using pharmaceutical composition which comprises administering to a patient an effective dose of ZPP and derivatives thereof; an effective amount of Y29794 and their derivatives; ZPP on combination with effective amount of rapamycin and its derivatives, and derivatives thereof; Y29794 in combination with effective amount of rapamycin and its derivatives thereof wherein the derivative is the compound of one or more chemical reactions resulting in modification of the parent compounds with derivatives of the parent compounds having a similar structure, having a similar effect on the function.

The invention also provides a method for treating or preventing abnormal activation of PI3K/AKT/mTOR signal pathway associated diseases, which comprises administering to a patient an effective dose of an antagonist of PRCP, or an effective dose of PREP antagonist, and an effective amount of PRCP and PREP dual antagonists, and joint use of mTOR antagonists with effective dose of PRCP antagonist, the joint use of an effective dose PREP antagonists and mTOR antagonists, the joint use of an effective dose of PRCP and PREP dual antagonists and an mTOR antagonist. mTOR antagonists include antagonists of mTOR as well as antagonists of molecules directly upstream and downstream of mTOR signal transduction.

PREP and PRCP chemical antagonists include (tert-butyl (2s)-2-{[(2s)-2-formylpyrrolidin-1-yl]carbonyl}pyrrolidine-1-carboxylate) (Z-Pro-Prolinal or ZPP), and derivatives thereof. In a particular embodiment, ZPP inhibits P13K kinase activity and phosphorylation of AKT, ZPP also inhibits rapamycin-induced feedback activation of IRS-1, PI3K and AKT. ZPP is a prolinal compound. Currently ZPP and derivatives thereof as inhibitors and the production method is disclosed, for example, reference to U.S. Pat. No. 5,411, 976. ZPP derivatives include, but are not limited to benzyl(2S)-2-[(2S)-2-formylpyrrolidine-1-carbonyl]pyrrolidine-1-carboxylate (Z-Pro-Pro-dimethyl acetal aldehyde); terephthalic acid bis(L-prolyl-pyrrolidine)amide; tert-butyl(2S)-2-(pyrrolidin-1-ylcarbonyl)pyrrolidine-1-carboxylate; UAMC -00021; 4-phenyl-1-[(2S)-2-(pyrrolidine-1-carbonyl)pyrrolidin-1-yl]butan-1-one (SUAM 1221); ((S)-2-[[(S)-2-(hydroxyacetyl)-1-pyrrolidinyl]carbonyl]-N-phenylmethyl)-1-pyrrolidinecarboxamide) (JTP-4819).

PREP chemical antagonists include [2-[8-(dimethylamino)octylsulfanyl]-6-propan-2-ylpyridin-3-yl]-thiophen-2-ylmethanone (Y29794) and its derivatives. In one particular embodiment of the present invention, Y29794 induces IRS-1 serine phosphorylation and degradation, inhibiting PI3K kinase activity and phosphorylation of AKT, Y29794 also inhibits rapamycin-induced feedback activation of IRS-1, PI3 and AKT.

Y29794 is a pyridine compound. Currently Y29794 and derivatives thereof as inhibitors and the production method is disclosed, for example, in reference to U.S. Pat. No. 5,001,137. Y29794 derivatives include (but not limited to) [2-[6-(dipropylamino)hexylsulfanyl]-6-propan-2-ylpyridin-3-yl]-thiophen-2-ylmethanone; [2-[6-(dimethylamino)hexylsulfanyl]-6-(2-methylpropyl)pyridin-3-yl]-thiophen-2-ylmethanone; [2-[6-(dimethylamino)hexylsulfanyl]-6-(3-methylbutyl)pyridin-3-yl]-thiophen-2-ylmethanone; [2-[6-(dimethylamino)hexylsulfanyl]-6-propan-2-ylpyridin-3-yl]-(5-methylthiophen-2-yl)methanone; [2-[6-(diethylamino)hexylsulfanyl]-6-propan-2-ylpyridin-3-yl]-thiophen-2-ylmethanone; [2-[6-(dimethylamino)hexylsulfanyl]-6-propan-2-ylpyridin-3-yl]-thiophen-2-ylmethanone; [2-[6-(dimethylamino)hexylsulfanyl]-6-propylpyridin-3-yl]-thiophen-2-ylmethanone; [2-[6-[2-(dimethylamino)ethyl-methylamino]hexylsulfanyl]-6-propan-2-ylpyridin-3-yl]-thiophen-2-ylmethanone; [2-[6-[benzyl(methyl)amino]hexylsulfanyl]-6-propan-2-ylpyridin-3-yl]-thiophen-2-ylmethanone; [6-tert-butyl-2-[6-(dimethylamino)hexylsulfanyl]pyridin-3-yl]-thiophen-2-ylmethanone; [2-[6-(dimethylamino)hexylsulfanyl]-6-methylpyridin-3-yl]-thiophen-2-ylmethanone; [2-[6-(dimethylamino)hexylsulfanyl]-4,6-dimethylpyridin-3-yl]-thiophen-2-ylmethanone; [2-[6-(butylamino)hexylsulfanyl]-6-propan-2-ylpyridin-3-yl]-thiophen-2-ylmethanone; [2-[6-(4-benzylpiperidin-1-yl)hexylsulfanyl]-6-propan-2-ylpyridin-3-yl]-thiophen-2-ylmethanone; [2-[8-(methylamino)octylsulfanyl]-6-propan-2-ylpyridin-3-yl]-thiophen-2-ylmethanone; [2-[6-(methylamino)hexylsulfanyl]-6-propan-2-ylpyridin-3-yl]-thiophen-2-ylmethanone; [2-[6-(tert-butylamino)hexylsulfanyl]-6-propan-2-ylpyridin-3-yl]-thiophen-2-ylmethanone; [6-propan-2-yl-2-[6-(propan-2-ylamino)hexylsulfanyl]pyridin-3-yl]-thiophen-2- ylmethanone; [2-[6-(ethylamino)hexylsulfanyl]-6-propan-2-ylpyridin-3-yl]-thiophen-2-ylmethanone; (E)-but-2-enedioic acid; [2-[6-(dimethylamino)hexylsulfanyl]-6-(3-methylbutyl)pyridin-3-yl]-thiophen-2-ylmethanone; [2-[6-(benzylamino)hexylsulfanyl]-6-propan-2-ylpyridin-3-yl]-thiophen-2-ylmethanone; [2-[6-(2-phenylethylamino) hexylsulfanyl]-6-propan-2-ylpyridin-3-yl]-thiophen-2-ylmethanone; [2-[8-(dimethylamino)octylsulfanyl]-6-propan-2-ylpyridin-3-yl]-thiophen-2-ylmethanone; oxalic acid; [2-[6-(dimethylamino)hexylsulfanyl]-6-propan-2-ylpyridin-3-yl]-thiophen-2-ylmethanone; oxalic acid; [2-[6-(diethylamino)hexylsulfanyl]-6-propan-2-ylpyridin-3-yl]-thiophen-2-ylmethanone; oxalic acid; [2-[6-(dimethylamino)hexylsulfanyl]-6-propan-2-ylpyridin-3-yl]-(5-methylthiophen-2-yl)methanone; oxalic acid; [2-[6-(dimethylamino)hexylsulfanyl]-6-propan-2-ylpyridin-3-yl]-phenylmethanone; [2-[6-(dimethylamino)hexylsulfanyl]-6-propylpyridin-3-yl]-thiophen-2-ylmethanone; oxalic acid; N,N-diethyl-2-methyl-6-thiophen-3-ylpyridine-3-carboxamide; N-(cyclopropylmethyl)-N,2-dimethyl-6-thiophen-3-ylpyridine-3-carboxamide; [6-propan-2-yl-2-[6-[4-[3-(trifluoromethyl)phenyl]piperazin-1-yl]hexylsulfanyl]pyridin-3-yl]-thiophen-2-ylmethanone; [2-[6-(dimethylamino) hexylsulfanyl]pyridin-3-yl]-(5-ethylthiophen-2-yl) methanone; [2-[6-[4-[bis(4-fluorophenyl)methyl]piperidin-1-yl]hexylsulfanyl]-6-propan-2-ylpyridin-3-yl]-thiophen-2-ylmethanone; [2-[6-[benzyl(methyl)amino]hexylsulfanyl]-6-propan-2-ylpyridin-3-yl]-thiophen-2-ylmethanone; oxalic acid; [6-tert-butyl-2-[6-(dimethylamino)hexylsulfanyl]pyridin-3-yl]-thiophen-2-ylmethanone; oxalic acid; [2-[6-(dimethylamino)hexylsulfanyl]-6-methylpyridin-3-yl]-phenylmethanone; [2-[8-(dimethylamino)octylsulfanyl]-6-propan-2-ylpyridin-3-yl]-thiophen-2-ylmethanone; 4-methylbenzenesulfonic acid; [4-[(dimethylamino)methyl]piperidin-1-yl]-(2-methyl-6-thiophen-3-ylpyridin-3-yl) methanone; (2-methyl-6-thiophen-3-ylpyridin-3-yl)-piperidin-1-ylmethanone; N-(2-cyanopropyl)-N-ethyl-2-methyl-6-thiophen-3-ylpyridine-3-carboxamide; N,N,2-trimethyl-6-thiophen-3-ylpyridine-3-carboxamide; (2-methyl-6-thiophen-3-ylpyridin-3-yl)-thiomorpholin-4-ylmethanone; N,N,6-trimethyl-2-[1-(thiophen-3-ylmethyl)piperidin-4-yl]pyridine-3-carboxamide; [2-[1-[2-[bis(4-fluorophenyl) methyl]piperidin-1-yl]hexylsulfanyl]-6-propan-2-ylpyridin-3-yl]-thiophen-2-ylmethanone; [2-[5-(dimethylamino) pentylsulfanyl]pyridin-3-yl]-thiophen-2-ylmethanone; [2-[6-(butylamino)hexylsulfanyl]-6-propan-2-ylpyridin-3-yl]-thiophen-2-ylmethanone; oxalic acid; [2-[6-(ethylamino) hexylsulfanyl]-6-propan-2-ylpyridin-3-yl]-thiophen-2-ylmethanone; oxalic acid; [2-[6-(dipropylamino) hexylsulfanyl]pyridin-3-yl]-thiophen-2-ylmethanone; [2-[1-[6-(dimethylamino)hexylsulfanyl]-2-methylpropan-2-yl]sulfanylpyridin-3-yl]-thiophen-2-ylmethanone; [2-[8-(dimethylamino)octan-2-ylsulfanyl]pyridin-3-yl]-thiophen-2-ylmethanone; [2-[7-(dimethylamino)heptan-2-ylsulfanyl]pyridin-3-yl]-thiophen-2-ylmethanone; [2-[6-(dimethylamino)hexan-2-ylsulfanyl]pyridin-3-yl]-thiophen-2-ylmethanone; [2-[7-(dimethylamino)heptylsulfanyl]pyridin-3-yl]-thiophen-2-ylmethanone; [2-[2-[3-(dimethylamino)propylsulfanyl]ethylsulfanyl]pyridin-3-yl]-thiophen-2-ylmethanone; [2-[1-[3-(dimethylamino) propylsulfanyl]propan-2-ylsulfanyl]pyridin-3-yl]-thiophen-2-ylmethanone; [2-[2-[6-(dimethylamino)hexylsulfanyl] ethylsulfanyl]pyridin-3-yl]-thiophen-2-ylmethanone; [2-[1-[6-(dimethylamino)hexylsulfanyl]propan-2-ylsulfanyl]pyridin-3-yl]-thiophen-2-ylmethanone; [2-[6-(dimethylamino)hexylsulfanyl]pyridin-3-yl]-thiophen-2-ylmethanone.

mTOR chemical antagonists include rapamycin and rapamycin derivatives. Rapamycin (also sirolimus) is a known macrolide, its chemical name is (3S,6R,7E,9R,10R,12R,14S,15E,17E,19E,21S,23S,26R,27R,34aS)-9,10,12,13,14,21,22,23,24,25,26,27,32,33,34,34a-hexadecahydro-9,27-dihydroxy-3-[(1R)-2-[(1S,3R,4R)-4-hydroxy-3-methoxycyclohexyl]-1-methylethyl]-10,21-dimethoxy-6,8,12,14,20,26-hexamethyl-23,27-epoxy-3H-pyrido [2,1-c][1,4]oxaazacyclohentriacontine-1,5,11,28,29 (4H,6H,31H)-pentone. mTOR antagonists also include rapamycin derivatives. Rapamycin and its derivatives as antagonists of mTOR chemistry are disclosed, for example, in reference to U.S. Pat. Nos. 3,993,749, 6,277,983, 7,384,953, Chinese Patent No. 200980154352.X. Many derivatives of rapamycin are known in the art. Rapamycin derivative examples include, but are not limited to, everolimus, tacrolimus, CCI-779, ABT-578, AP-23675, AP-23573 AP-2384 7-Table-rapamycin Su 7-thiomethyl rapamycin 7-Table-trimethoxyphenyl-rapamycin 7-Table-thiomethyl-rapamycin 7-to methoxy-rapamycin ADM 32-to methoxy-rapamycin 2-demethylation-rapamycin, before rapamycin (prerapamycin), temsirolimus matter (temsirolimus) and 42-0-(2-hydroxy)ethyl-rapamycin. Other derivatives of rapamycin include: oximes of rapamycin (U.S. Pat. No. 5,446,048), the amino esters of rapamycin (U.S. Pat. No. 5,130,307), two rapamycin aldehyde (U.S. Pat. No. 6,680,330), rapamycin 29-enolase (U.S. Pat. No. 6,677,357), 0-Dyke glycosylation (U.S. Pat. No. 6,440,990 rapamycin derivatives), water-soluble esters of rapamycin (U.S. Pat. No. 5,955,457), alkyl with rapamycin derivatives (U.S. Pat. No. 5,922,730), amidino carbamates of rapamycin (U.S. Pat. No. 5,637,590), rapamycin biotin esters (U.S. Pat. No. 5,504,091), carbamates of rapamycin (U.S. Pat. No. 5,567,709), the hydroxy ester of rapamycin (U.S. Pat. No. 5,362,718), rapamycin 42-sulfonate and 42-(N-oxy-chi Dyke) amino acid esters (U.S. Pat. No. 5,346,893), rapamycin epoxycyclohexane alkyl isomers (U.S. Pat. No. 5,344,833), imidazolidine derivatives of rapamycin (U.S. Pat. No. 5,310,903), alkoxyalkyl esters of rapamycin (U.S. Pat. No. 5,233,036), pyrazole rapamycin (U.S. Pat. No. 5,164, 399), acyl derivatives of rapamycin (U.S. Pat. No. 4,316,885), the reduction product of rapamycin (U.S. Pat. Nos. 5,102,876 and 5,138,051), amide esters of rapamycin (U.S. Pat. No. 5,118,667), fluorinated esters of rapamycin (U.S. Pat. No. 5,100,883), acetal rapamycin (U.S. Pat. No. 5,151,413), oxa-rapamycin (U.S. Pat. No. 6,399,625), and silyl ethers of rapamycin (U.S. Pat. No. 5,120,842).

The present invention is a pharmaceutical composition comprising rapamycin and its derivatives, and ZPP and derivatives thereof. Another present invention is a pharmaceutical composition comprising rapamycin and derivatives thereof, and Y29794 and derivatives thereof.

Below with reference to specific embodiments, the present invention will be further elaborated. The following examples illustrate preferred embodiments of the present invention. The skilled person will appreciate that, in the embodiment of the present invention showed good technique disclosed embodiment represent techniques discovered by the inventors in the following examples, and therefore it can be considered to constitute preferred modes. However, it should be understood that these examples are intended to illustrate the invention and not to limit the scope of the invention. According to the present specification, the skilled person will understand that many modifications and changes may be made to the present invention without departing from the spirit of the scope of the disclosed embodiment, and still obtain a like or similar result. A person skilled in the art understands the conventional method described in the experimental method described below, if no special instructions are presented or materials used; if no special instructions are presented, routine biochemical reagents were purchased. In a particular embodiment, PRCP and PREP plays a necessary role in PI3K/AKT/mTOR signaling activation and proliferation and survival of cancer cells.

By including breast cancer cell lines MCF7 and TD47, pancreatic cancer cell line Panc-1, PK-9, Capan-1 and AsPC-1, and lung cancer cell lines A549 and H1703 presented results indicate that gene silencing of PREP or PRCP decreases proliferation of cancer cells, and dual silencing of gene expression PREP and PRCP causes proliferation arrest of cancer cells. The present invention indicates that specifically inhibiting PRCP or PREP gene expression, dual inhibition of gene expression PREP and PRCP reduce IRS-1, PI3K and AKT activity, and prevents rapamycin-induced feedback activation of IRS-1, PI3K and AKT. In another particular embodiment, the inhibitory effect of ZPP and Y29794 on PI3K/AKT/mTOR signaling pathway and cancer cell proliferation and survival show that ZPP or Y29794 stop the proliferation of cancer cells. ZPP or Y29794 reduce insulin receptor substrate (IRS-1) protein, thereby inhibiting PI3K and AKT activity. ZPP or Y29794 prevents rapamycin-induced feedback increase in insulin receptor substrate (IRS-1), thereby inhibiting the activity of PI3K and AKT. And, ZPP or Y29794 in combination with rapamycin together have a synergistic effect on inhibition of cancer cell proliferation and survival. Y29794 inhibits pancreatic tumor growth in tumor xenograft experiments in immunodeficient mice. Y29794 in combination with rapamycin has synergistic effect in inhibition of tumor growth.

Example 1

ZPP and Y29794 Induces Cytotoxicity in Cancer Cells 1.1. ZPP and Y29794 induces cytotoxicity to cancer cells by MTT analysis of cell viability. Cells were placed in 96-well plates (3×10 cells/well) in octuplicate. The cells were then treated with vehicle or different doses of ZPP for 4 days. Cells were then loaded with 1.2 mM MTT (4,5-Dimethylthiazol-2-vn-2,5-diphenyltetrazolium bromide, a yellow tetrazole) in phenol red-free medium for 4 hours. The cells were then lysed in 10% SDS/0.01M HCL. MTT absorbance (570 nm spectrum) was measured by a microplate reader. The relative absorbance is normalized to the control (vehicle-treated) to indicate relative cell viability. ZPP was purchased from Biomol (Plymouth Meeting, Pa., USA). MTT was purchased from Sigma-Aldrich. Panc-1 and Capan-1 pancreatic cancer cell line, MCF7 and T47D breast cancer cell lines, A549 and HI 703 lung cancer Cell lines were purchased from American Type Culture Collection (ATCC, USA) preparation of pancreatic cancer cell line PK-9 have been disclosed, e.g., Kobari M et al, (1986) Tohoku J Exp Med. 150: 231-248; Etoh T et al, (2003) Clin Cancer Res 9; 1218; Arafat H. et al, (2011) Surgery 150 (2): 306-315. Cells were grown in Dulbecco's Modified. Eagle's (DMEM) medium (Invitrogen, Carlsbad, Calif.) containing 10% fetal bovine serum (FBS) (Hyclone, purchased from Thermo Fisher Scientific, Inc). Results indicate that ZPP decreases MTT absorbance in a dose dependent manner in pancreatic cancer cell lines Panc-1, PK-9, Capan-1 and AsPC-1 (FIG. 1A), lung cancer cell lines H1703 and A549 (FIG. 1B), and breast cancer cell lines MCF7 and TD47 (FIG. 1C), indicating ZPP is cytotoxic to cancer cells. In similar experiments, the cells were treated with different doses of Y29794 for 4 days and analyzed for MTT absorbance. Y29794 oxalate was purchased from Tocris Biosciences (Bristol, UK). The results show that in pancreatic cancer cell lines Panc-1, PK-9, Capan-1 and AsPC-1 (FIG. 2A), lung cancer cell line H1703 and A549 (FIG. 2B), and breast cancer cell lines MCF7, TD47 and MDAMB231 (FIG. 2C), Y29794 shows a dose-dependent cytotoxicity to cancer cells.

1.2. Colony formation assay (clonogenic assay) was used to analyze the effect of ZPP or Y29794 on cancer cell survival. $10^3$ Panc-1 cells were plated in 100 mm petri dish in triplicate fed with 10 ml of DMEM containing 10% FBS. The cells were then treated by ZPP for 7 days and cultured for additional three weeks. Cells were then rinsed three times with PBS, fixed with 100% ethanol for 15min, and stained with 2% crystal violet ethanol solution. The stained colonies were counted. All the results are statistically analyzed by one way ANOVA and two tailed t-test. The results showed that ZPP significantly ($P<0.01$) decreased Panc-1 pancreatic cancer cell survival (FIG. 1D).

Example 2

PRCP and/or PREP Gene Silencing Inhibits Cancer Cell Proliferation 2.1. Lentiviral shRNA silencing of PREP and/or PRCP genes in cancer cells Lentiviral vector (pLKO. 1) with PREP shRNA (PREP shRNA #1 clone identification number TRCN0000050198; PREP shRNA #2 clone identification number TRC0000050199) and PRCP shRNA (PRCP shRNA #1 clone identification number TRCN0000050808; PRCP shRNA #2 clone identification number TRC0000050809) were purchased from OpenBiosystems (USA). pLKO. 1 with shRNA plasmids and viral packaging vectors psPAX2 and pMD2G (purchased from Addgene (Cambridge, Mass., USA) plasmids were used for PRCP and PREP gene silencing. Viral packaging cells 293FT were purchased from Invitrogen Corporation (Carlsbad, Calif., USA). Specific methods: (1) Generating viral supernatant of PREP shRNA or PRCP shRNA: $5\times10^5$ 293FT viral packaging cells were placed in 100 mm petri dish in 10 ml of DMEM containing 10% FBS. The next day, 6 micrograms of plasmid of PRCP shRNA (or PREP shRNA), 3 micrograms of the psPAX2 plasmid, and 6 micrograms of pMD2.G plasmid DNA were mixed in 500 microliters of culture medium with 45 microliters of Fugene transfection reagent (Promega Corp, Madison, Wis., USA) for 15 minutes. This mixture was then added to the 293FT packaging cells. On the third day, the supernatant containing viruses was collected and filtered through a 0.45 micron syringe filter; (2) viral infection of the experimental cells: $5\times10^5$ experimental cells (e.g., pancreatic carcinoma cell line Panc-1, PK-9, Capan-1, and MCF7 breast cancer cell lines, etc.) were placed in 100 mm petri dishes. 5 ml viral supernatant was mixed with 5 ml culture medium and added to the cells. After 24 hours, puromycin (1 μg/ml) was added to the medium for selection of the infected cells. One week after selection the cells were used for further experiments.

2.2 Immunoblot analysis of gene silencing of PRCP or PREP in cancer cells. Mouse anti-PRCP antibody was purchased from Abeam (Cambridge, Mass., USA). Goat anti-PREP antibody was purchased from R&D Systems (Minneapolis, Minn., USA). Mouse anti-β-actin antibody antibodies was from Santa Cruz Biotechnology (Santa Cruz, Calif., USA). Panc-1 pancreatic cancer cells and MCF7 breast cancer cells were cultured to 80% confluence, cells were rinsed three times with pre-cooled PBS, 500 µl of lysis buffer (150 mmol/L Nacl, 1% Triton-x-100, 50 mmol/l Tris pH 8.0, 1 mmol/L PMSF, 1 ug/L aprotinin. 1 ug/L leupeptin, 1 ug/L peptain) was added to the cells. Cells were scraped and transferred to a centrifuge tube with a pipette. The lysates were spun in a microcentrifuge at maximal speed for 10 minutes at 4° C. to get rid of the insoluble fraction. Protein concentration was determined by Bradford assay. For immunoprecipitation: 2-5 ug protein-specific antibodies were added to 250-500 ug of lysates in a tube and incubated on an ordital shaker 4° C. for 2-4 hours with moderate shaking, then 20 ul Protein G beads (Santa Cruz Biotechnology (Santa Cruz, Calif., USA.) were added and the mixture was incubated with moderate shaking for another hour. After washing the beads in lysis buffer five times, the immunoprecipitates were boiled in 2x Laemmli sample buffer (50 mmoL/L Tris-HCL (pH 8.0), 100 mmoL/L DTT, 2% SDS, 0.1% bromophenol blue, 10% glycerol) for five minutes. The proteins were separated by conventional SDS-polyacrylamide gel electrophoresis (SDS-PAGE) electrophoresis and transferred to Amersham Hybond-P PVDF membrane (GE Company, Pittsburgh, Pa., USA). For immunoblot, the membrane was blocked in 2% BSA in TBST buffer (Tris 1.21 g+NaC15.84 g+800 ml H$_2$O adjusted to pH 8.0 with HC1) for one hour and then incubated with primary antibodies in TBST at room temperature (22-25° C.) for 2 hours. After washing three times with TBST, the membrane was incubated with HRP-conjugated secondary antibodies for 0.5 hours at room temperature. After washing the membrane five times with TBST (5 minutes/each), the membrane was incubated with ECL chromogenic reagent (GE Company, Pittsburgh, Pa., USA) for 1-5 minutes. The blots were exposed to films in darkroom for 1-5 minute. The films were developed in an automatic X-OMAT Developer (KODAK, Rochester, N.Y., USA). The results show that in the cells with stable silencing of PREP (PREP KD) or PRCP (PRCP KD) or both PREP and PRCP (DKD), expression of PREP or PRCP proteins were reduced (FIGS. 3B and C). PREP gene silencing (PREP KD) or PRCP gene silencing (PRCP KD) or gene silencing both PRCP and PREP (DKD) in MCF7 cells reduces expression of PREP and/or PRCP proteins compared with control cells (control) (FIGS. 6B & C). Thus, in Panc-1 and MCF7 cells, PRCP gene silencing, PREP gene silencing or PRCP and PREP gene silencing successfully reduced expression of PRCP and/or PREP proteins in the cells.

2.3 Real-Time Quantitative PCR Analysis of PRCP or PREP Gene Expression in Cancer Cells with PRCP and/or PREP Gene Silencing.

Trizol, superscript III first-strand synthesis supermix, SybrGreen qPCR supermix was purchased from Invitrogen (Carlsbad, Calif., USA). PRCP primers (Forward: TCTA-CACTGGTAATGAAGGGGAC (shown as SEQ ID No.3), reverse: TCCTTGAATGAGTTGTCACCAAA (shown as SEQ ID No.4)). PREP primers (forward: GAGACCGCCG-TACAGGATTAT (shown as SEQ ID No.5), reverse: TGAAGTGGCAACTATACTTGGGA (shown as SEQ ID No.6) were synthesized by Integrated DNA Technologies Company (Coralville, Iowa, USA). Specific methods: (I) fotal RNA extraction: pancreatic cancer cells PK-9 and Capan-1 at 80% confluence were rinsed with ice-cold PBS three times, lysed in 1 ml Trizol at RT for 5 min and then mixed with 0.2 ml of chloroform for 2 to 3 min. The mixture was centrifuged at 12000 g at 4° C. for 15 min. The supernatant (approximately 0.6 ml) was transferred to a new tube with addition of 0.6 ml chloroform and incubate at RT for 2 min and then centrifuged for another 15 min (secondary chloroform extraction). Equal volume of isopropanol was added to the supernatant to precipitate RNA by centrifugation at 12000 g for 10 min. The precipitates were washed with 1 ml 75% of DEPC-ETOH and centrifuged for 5 min. RNA was dried and dissolved in water. RNA concentration and purify was determined by measuring $A_{260}/A_{280}$ and $A_{260}/A_{230}$ values, (2) First strand cDNA synthesis (superscript III supermix, Thermo Fisher, Grand Island, N.Y., USA): 2XRT reaction mix 10 µl, RT enzyme mix 2 RNA (1 µg), nuclease-free water, total volume 20 µl. Gently mix, 25° C. incubation 10 min, 37° C. incubation 120 min, 85° C. 5 min, and then placed on ice, (4) qPCR reaction (SybrGreen qPCR Master Mix, Applied Biosystems, Warrington, UK)): Mixed SybrGreen supermix universal 2×10 µl, forward primer (4 µM) in a PCR tube 1 µl, reverse primer (4 µM) 1 µl, cDNA. (1 µg from total RNA) 1 µl, nuclease-free water to 20 µl reacted on real-time PCR instrument (Thermo Fisher, Grand Island, N.Y., USA) with standard procedure: 50° C. 2 min, 95° C. 10 min, 40 cycle: 95° C. 15 s, 60° C. 60 s. Relative abundance of cDNA was calculated by standard curve method. The PCR results showed that PRCP and/or PREP mRNA was reduced in PK-9 cells (FIG. 4B) and Capan-1 cells (FIG. 5B) with gene silencing of PRCP (PRCP KD), PREP (PREP KD), or both PRCP and PREP (DKD) compared to control cells (control).

2.4 Cell proliferation assay by staining cellular DNA in cells with gene silencing of PRCP, PREP, and both of PREP and PRCP. Cells were placed in 96-well plates (3×10$^3$ cells/well) in octuplicate. All cells were grown in DMEM containing 10% FBS. Medium was refreshed every two days. Cells were harvested at day one, day four and day seven by freezing and thawing in 100 µl of TE (pH 8) buffer after removing medium and rinsing with PBS for three times, Cellular DNA was stained with Picogreen (Invitrogen, Grand Island, N.Y., USA) in 1:200 dilution in TE buffer for 30 min, the fluorescence was measured by a microplate reader with excitation/emission at 480 nm/520 nm). Relative fluorescence intensity of Picogreen (average from octuplicate) was normalized to cells harvested at day 1 to indicate cell proliferation. Compared to control cells (control), pancreatic cancer cell lines Panc-1 (FIG. 3A), PK-9 (FIG. 4A), Capan-1 (FIG. 5A) and breast cancer cell line MCF7 (FIG. 6A) with gene silencing of PRCP (PRCP KD1 and PRCP KD2) and/or PREP (PREP KD1 and PREP KD2) show reduced proliferation.

Example 3

Gene Silencing of PREP and PRCP Genes, ZPP or Y29794 Treatment Decreases IRS-1, PI3K and AKT Activity and Blocks Rapamycin-Induced Feedback Activation of IRS-1 and AKT 3.1 Reduction in AKT phosphorylation is examined by immunoblot using rabbit anti-phospho-AKT (S437) and rabbit anti-pan AKT antibodies purchased from Cell Signaling Technology (Danvers, Mass., USA) in the cells with gene silencing of PRCP and/or PREP or treated with ZPP or Y29794. Reduction in PRCP and/or PREP is shown by Western blot and quantitative PCR described in 2.2.

Immunoblot analysis of cell lysates of PK-9 (FIG. 7A), Capan-1 (FIG. 7B) and Panc-1 (FIG. 7C) by comparing control cells (control) to the cells with PRCP gene silencing (PRCP-KD1) or PREP gene silencing (PREP-KD1) or double PRCP and PREP gene silencing (DKD) show that phosphorylated AKT (p-AKT) was significantly reduced in the cells with gene silencing of PRCP and PREP. MCF7 cell lysates by immunoblot analysis (FIG. 7D) show that phosphorylation of AKT is also significantly reduced by gene silencing of both PRCP and PREP (DKD) compared to control cells (control).

Figure 8A:
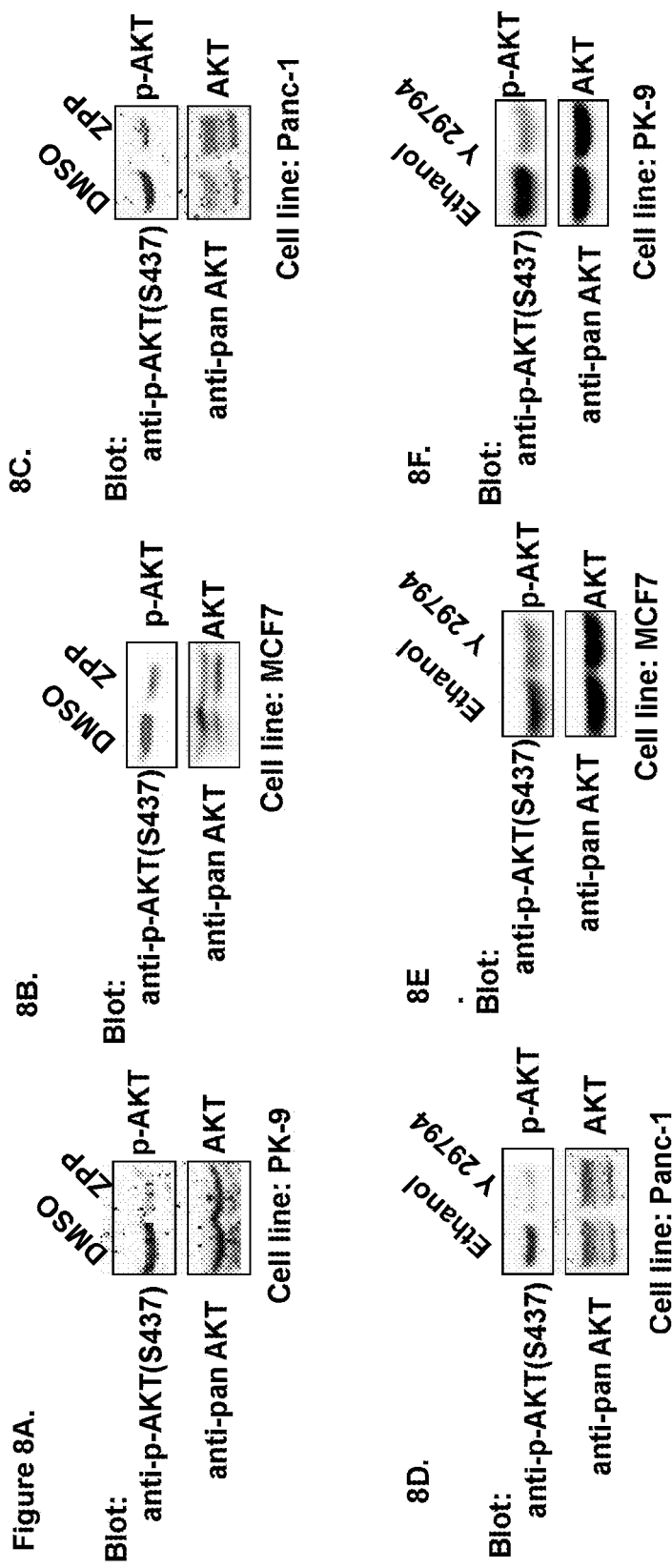
FIG. 8A reports reduced AKT phosphorylation (S473) in PK-9 cells treated with ZPP (400 µM) compared with cells treated with vehicle (DMSO).

PK-9 (FIG. 8A), Capan-1 (FIG. 8B) and Panc-1 (FIG. 8C) were treated with ZPP (200 µM) for two days. Immunoblot analysis of cell lysates shows that AKT phosphorylation in ZPP treated cells is significantly decreased compared to vehicle (DMSO) treated cells. Panc-1 (FIG. 8D), MCF7 (FIG. 8E) and PK-9 (FIG. 8F) were treated with Y29794 (0.5 µM) for two days. Immunoblot analysis of cell lysates shows that AKT phosphorylation in Y29794 treated cells is significantly decreased compared to vehicle (ethanol) treated cells.

3.2 AKT phosphorylation was examined by immunoblot as described in 3.1. IRS-1 expression was analyzed by immunoblot using anti-IRS-1 antibodies purchased from Santa Cruz Biotechnology (Santa Cruz, Calif., USA). Reduction in PRCP and/or PREP by gene silencing is shown by Western blot and quantitative PCR described in 2.2.

Figure 9:
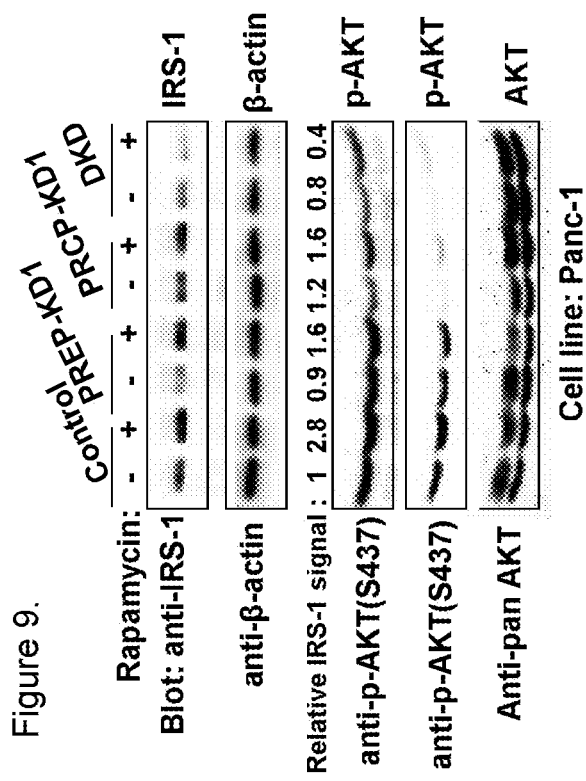
FIG. 9. Immunoblot analysis of IRS-1 expression and AKT phosphorylation in Panc-1 cells: figure reports that expression of IRS-1 is reduced and phosphorylation of AKT is inhibited by gene silencing of PRCP and PREP.

Panc-1 cells were treated with rapamycin (10 nM) for 24 hours and cell lysates were immunoblotted for IRS-1 and phospho-AKT and AKT. In control cells, rapamycin treatment significantly increased IRS-1. protein and AKT phosphorylation. In cells with silenced PRCP gene (PRCP KD (FIG. 9)), or cells with silenced PREP gene (PREP KD (FIG. 9)), the increase in IRS-1 and phospho-AKT induced by rapamycin was slightly lower than the control cells. In cells with both PRCP and PREP genes silenced (DKD (FIG. 9)), rapamycin-induced increase in IRS-1 and phospho-AKT was significantly lower than that in control cells.

Panc-1 cells (FIG. 10A) and MCF7 (FIG. 10B) cells were treated with vehicle, rapamycin (10 nM), ZPP (200 µM) or rapamycin plus ZPP for 24 hours. Cell lysates were immunoblotted for phospho-AKT, AKT, IRS-1, and β-actin. Rapamycin induced an increase in IRS-1 and phosphorylation of AKT, which was blocked by ZPP treatment. In another experiment, Panc-1 cells (FIG. 11A) and MCF7 (FIG. 11B) cells were treated with vehicle, rapamycin (10 nM), Y29794 (0.5 µM) or rapamycin plus Y29794 for 24 hours. Cell lysates were immunoblotted for phospho-AKT, AKT, IRS-1, and β-actin. Rapamycin induced an increase in IRS-1 and phosphorylation of AKT, which was blocked by Y29794 treatment.

Figure 12:
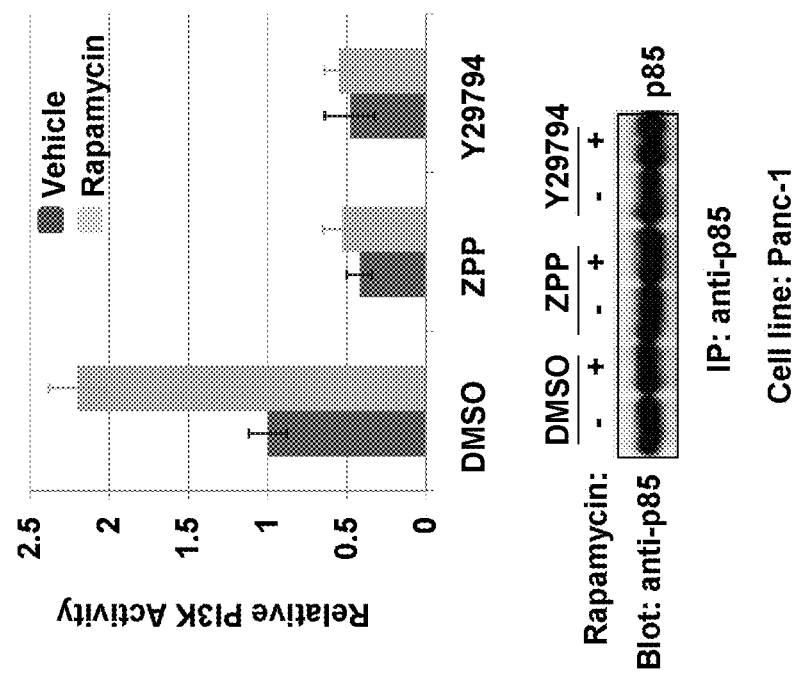
FIG. 12.

3.3 PI3K activity as well as rapamycin-induced feedback increase in PI3K activity is inhibited by gene silencing of PRCP and PREP or treatment with ZPP or Y29794 by PI3K kinase assay PI3K kinase assay kit (Calbiochem, Bilerica, Mass., USA) was used to measure the IRS-1-associated or p85-associated PI3K kinase activity in cells. The indicated cells were treated with different conditions for 24 hours. The cells were rinsed three times with pre-cooled PBS, lysed in 500 µl of lysis buffer (150 mmol/L Nacl, % Triton-x-100, 50 mmol/l Tris (pH8.0, 1 mmol/L PMSF, 1 µg/L aprotinin, 1 µg/L leupeptin, 1 µg/L peptain). Cell lysates (500 µg, in triplicate) of were used for anti-IRS-1 or anti-p85 immunoprecipitation. The immunoprecipitates were resuspended in 200 µl assay buffer and mixed with the fluorescence-labeled PI3K substrate BODIPY-TMR-phosphatidylinositol (100 µM) and ATP (37° C.) for 1 hour. The fluorescence intensity was measured with a fluorometer (excitation wavelength of 540 nM, emission wavelength 570 nM). The difference between fluorescence intensity between control immunoprecipitates (no lysates) and lysate immunoprecipitates was used to indicate PI3K kinase activity. IR-1 anti-rabbit antibody and rabbit anti-PI3K p85 antibody were purchased from Millipore Corporation (Billerica, Mass., USA). Panc-1 anti-p85 immunoprecipitates were used for PI3K kinase assay (FIG. 12) and immunoblot analysis (FIG. 12). Rapamycin treatment in control cells increased PI3K kinase activity (P<0.01). In cells treated with ZPP (200 µM) PI3K kinase activity was significantly reduced (P<0.01), and rapamycin-induced increased in PI3K activity was inhibited by ZPP (P<0.01); in cells treated with Y29794 (0.5 µM) PI3K activity was significantly lower (P<0.01), Y29794 also inhibited rapamycin-.induced increase in PI3K kinase activity (P<0.01), anti-IRS-1 antibody (FIG. 14A) and anti-p85 PI3K antibody (FIG. 14B) was used to analyze PI3K kinase activity in Panc-1 cell lysates (FIG. 14) of in control cells and the cells with gene silencing of PRCP and PREP (DKD). In rapamycin treated control cells (control) the IRS-1 (FIG. 14A) and p85-associated PI3K activity was significantly elevated (FIG. 14B) (P<0.01). In the DKD cells IRS-1 (FIG. 14A) and p85 (FIG. 14B) associated PI3K activity were significantly reduced (P<0.01) compared to control cells. Rapamycin failed to induce significant increase in PI3K activity in DKD cells (FIG. 14B) (P>0.5).

Figure 13:
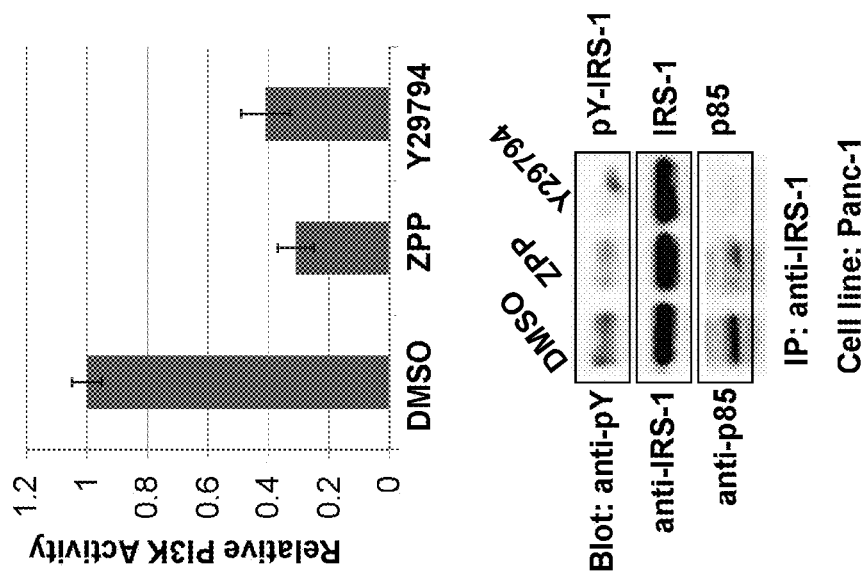
FIG. 13.

3.4 ZPP or Y29794 inhibits IRS-1 tyrosine phosphorylation and p85 PI3K subunit interaction with IRS-1 and PI3K kinase activity. Panc-1 cells were treated with ZPP (200 µM) or Y29794 (0.5 µM) for 24 hours. Lysates were immunoprecipitated with anti-IRS-1 antibodies and the anti-IRS-1 immunoprecipitates were used for PI3K kinase assay and anti-IRS-1 phospho-tyrosine and anti-p85 immunoblot analysis (FIG. 13). ZPP or Y29794 decreased IRS-1-associated PI3K activity (FIG. 13, upper) and tyrosine phosphorylation of IRS-1 and p85 (FIG. 13, lower).

Example 4

ZPP, Y29794, or its Combination with Rapamycin Induces Synergistic Cytotoxicity to Cancer Cells In Vitro 4.1 MTT cell viability assay and colony formation assay for evaluation of cytotoxic effect of ZPP and its combination with rapamycin.

Examples 1.1 MTT cell viability assay experiments and examples 1.2 colony-forming experiments to detect the combination of ZPP and rapamycin synergistically increased drug cytotoxicity. Panc-1 cells were treated with different doses of ZPP alone or in combination with rapamycin (0.5 nM) (FIG. 15A), or with different doses of rapamycin alone or in combination with ZPP (25 µM) (FIG. 15B) for four days. MTT assay showed that rapamycin significantly increased (P<0.01) ZPP-induced cytotoxicity (FIG. 15A), and vice versa, ZPP significantly (P<0.01) increased rapamycin-induced cytotoxicity (FIG. 15B). Colony formation assay (FIG. 15C) showed that rapamycin (1 nM and 10 nM) alone did not affect cell survival. ZPP (25 µM) in combination with rapamycin significantly (P<0.01) decreased cell survival.

4.2 MTT cell viability assay and colony formation assay for evaluation of cytotoxic effect of Y29794 and its combination with rapamycin.

Examples 1.1 MTT cell viability assay experiments and examples 1.2 colony-forming experiments to detect the combination of Y29794 and rapamycin synergistically increased drug cytotoxicity. Panc-1 cells were treated with different doses of Y29794 alone or in combination with rapamycin (0.5 nM) (FIG. 16A), or with different closes of rapamycin alone or in combination with Y29794 (25 nM) (FIG. 16B) for four days. MTT assay showed that rapamycin significantly increased (P<0.01) Y29794-induced cytotoxicity (FIG. 16A), and vice versa, Y29794 significantly (P<0.01) increased rapamycin-induced cytotoxicity (FIG. 16B). Colony formation assay (FIG. 16C) showed that rapamycin (1 nM and 10 nM) alone did not affect cell survival. Y29794 (25 nM) combination with rapamycin significantly (P<0.01) decreased cell survival.

Example 5

Y29794 Inhibits Pancreatic Tumor Growth and Combination of Y29794 with Rapamycin Synergistically Inhibits Tumor Growth 5:1 Analysis of therapeutic effect of Y29794 and its combination with rapamycin in xenotransplanted pancreatic tumor growth.

Figure 17:
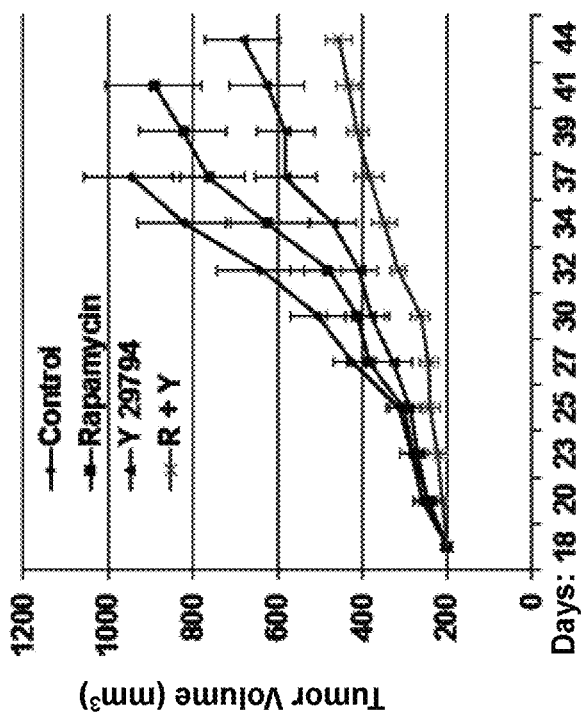
FIG. 17.

4-6 week-old male SCID mice (BALB/C) were purchased from Charles River laboratories (Wilmington, Mass., USA). Panc-1 cells at about 80% confluence were trypsinized with 0.25% trypsin and 0.02% EDTA. The cell suspension was centrifuged after addition of 10% FBS. $10^6$ cells were resuspended in 100 μl PBS buffer containing 10% Matrigel, and injected with a 1-cc syringe with a 27-30 sized needle into the right flank of nude mice under anesthesia. After tumor formation (mean volume 50-60 mm³) the mice were randomly divided into four groups (6 mice per group): control group, rapamycin treatment group, Y29794 treatment group, and Y29794 plus rapamycin treatment group. Rapamycin and Y29794 were dissolved in Cremophor formulation (20% Cremophor EL, 30% propylene glycol, 50% ethanol). Rapamycin (2 mg/kg body weight) was given by intraperitoneal injection one dose per week. Y29794 (20 mg/kg body weight) was administered by gavage five doses a week. Weekly measurements of tumor size (length, width and depth) and calculation of the tumor volume (½ larger diameter×(smaller diameter)) were carried until the control tumors reached 1000 mm³. The results (FIG. 17) showed that Y29794 alone significantly inhibited tumor growth (P<0.01). Combination of rapamycin with Y29794 inhibited tumor growth (P<0.01) more than Y29794 alone.

Example 6

PRCP and PREP Gene Silencing or Y29794 Induced IRS-1 Serine Phosphorylation and Degradation by Immunoblot Analysis As described in Example 2.2 and above, the cells with PRCP and PREP gene silencing were used for analysis of PRCP and PREP gene silencing and inhibition of serine phosphorylation and degradation of IRS-1 and its effects on response to rapamycin. The antibodies anti-IRS-1, anti-p-IRS (S307), anti p-IRS-1 (S636/639), anti p-S6K (T389), Anti-S6K, anti-insulin receptor (IR), insulin resistance like growth factor-1 receptor, anti-p-mTOR (S2448), anti-mTOR antibody was purchased from Cell Signaling (Denver, Mass., USA). The protein synthesis inhibitor cycloheximide (CHX) was purchased from Sigma Aldrich (TOWN, STATE, USA). Immunoblot analysis of cell lysates showed FIG. 18 that in cells with silencing of both PRCP and PREP genes (DKD in PK-9, Capan-1 and Panc-1 cells), insulin receptor substrate (IRS-1) protein was significantly reduced compared to control cells (control), while insulin-like growth factor receptor (IGF-1R) protein did not change (see FIG. 18A), indicating PRCP and PREP exclusively regulate IRS-1 but not IGF1R protein level. Compared to control cells, DKD cells show increased serine phosphorylation (S307 and S636/639) of IRS-1 alongside with decreased tyrosine phosphorylation of IRS-1 (FIG. 18B). To determine degradation of IRS-1, the cells were treated with CHX (20 μg/ml) to block protein synthesis for a time course. Immunoblot analysis of lysates showed that gene silencing of both PRCP and PREP genes shortened the half-life of IRS-1 compared to control cells, indicating that PRCP and PREP regulate the stability of IRS proteins (FIG. 18C). While rapamycin treatment stabilized IRS-1 in control cells by inhibiting serine 307 and serine 636/639 phosphorylation (FIG. 18C) silencing of both PRCP and PREP genes maintained phosphorylation of serine 636/639 and decreased IRS-1 stability, while rapamycin completely inhibited phosphorylation of S6K (T389) (FIG. 18D). The results indicate that PRCP and PREP inhibit serine phosphorylation and degradation of IRS-1. Similarly, inhibition of PREP/PRCP by Y29794 also induced serine phosphorylation and protein degradation of IRS-1 (see FIG. 19). Immunoblot analysis of Panc-1 cell lysates showed that, compared to control cells, Y29794-treated cells had significantly reduced IRS-1 protein (FIG. 19A) and increased serine phosphorylation (S307 and S636/639) of IRS-1 (FIG. 19B). Blocking protein synthesis by CHX in cells treated with Y29794 showed that Y29794 shortened half-life of IRS-1 (FIG. 19C) compared to vehicle treated cells (control). Moreover, while in control cells rapamycin induced increase in IRS-1 protein that was stable, in the cells treated with Y29794 IRS-1 protein was not increased nor stabilized by rapamycin, although rapamycin completely inhibited mTOR (S2448) phosphorylation.

Referred to herein and in any publication, references, patents and patent applications shall be deemed incorporated by reference in their entirety in this application, and should be regarded as based on a clear and independent way of reference in each individual publication, references, patents or patent applications. Any and all examples, or exemplary language provided herein (e.g., such as etc.) is intended merely to better illuminate the invention and does not form a restriction on the scope of the invention unless otherwise required. The present invention describes preferred embodiments, including the best mode known to the inventors for carrying out the invention. The preferred embodiments of the invention may include these variations, the present inventors intended to those specifically described herein various embodiments of the present invention, the same ordinary skill in the art are well aware of these changes and the expected variation can skillfully use. Can allow the legal scope of the present invention includes all modifications and equivalents of the appended claims, the subject matter referenced, unless otherwise indicated herein or clearly contradicted by context.

Sequences of PRCP, PREP, and primers used in Examples.

```
<210> 1
<211> 496
<212> PRT
<213> NP_005031 PRCP

<400> 1

Met Gly Arg Arg Ala Leu Leu Leu Leu Leu Ser Phe Leu Ala Pro
1               5                   10                  15
```

-continued

```
Trp Ala Thr Ile Ala Leu Arg Pro Ala Leu Arg Ala Leu Gly Ser Leu
     20                  25                  30

His Leu Pro Thr Asn Pro Thr Ser Leu Pro Ala Val Ala Lys Asn Tyr
 35                  40                  45

Ser Val Leu Tyr Phe Gln Gln Lys Val Asp His Phe Gly Phe Asn Thr
 50                  55                  60

Val Lys Thr Phe Asn Gln Arg Tyr Leu Val Ala Asp Lys Tyr Trp Lys
 65                  70                  75                  80

Lys Asn Gly Gly Ser Ile Leu Phe Tyr Thr Gly Asn Glu Gly Asp Ile
             85                  90                  95

Ile Trp Phe Cys Asn Asn Thr Gly Phe Met Trp Asp Val Ala Glu Glu
        100                 105                 110

Leu Lys Ala Met Leu Val Phe Ala Glu His Arg Tyr Tyr Gly Glu Ser
    115                 120                 125

Leu Pro Phe Gly Asp Asn Ser Phe Lys Asp Ser Arg His Leu Asn Phe
130                 135                 140

Leu Thr Ser Glu Gln Ala Leu Ala Asp Phe Ala Glu Leu Ile Lys His
145                 150                 155                 160

Leu Lys Arg Thr Ile Pro Gly Ala Glu Asn Gln Pro Val Ile Ala Ile
            165                 170                 175

Gly Gly Ser Tyr Gly Gly Met Leu Ala Ala Trp Phe Arg Met Lys Tyr
        180                 185                 190

Pro His Met Val Val Gly Ala Leu Ala Ala Ser Ala Pro Ile Trp Gln
    195                 200                 205

Phe Glu Asp Leu Val Pro Cys Gly Val Phe Met Lys Ile Val Thr Thr
210                 215                 220

Asp Phe Arg Lys Ser Gly Pro His Cys Ser Glu Ser Ile His Arg Ser
225                 230                 235                 240

Trp Asp Ala Ile Asn Arg Leu Ser Asn Thr Gly Ser Gly Leu Gln Trp
            245                 250                 255

Leu Thr Gly Ala Leu His Leu Cys Ser Pro Leu Thr Ser Gln Asp Ile
        260                 265                 270

Gln His Leu Lys Asp Trp Ile Ser Glu Thr Trp Val Asn Leu Ala Met
    275                 280                 285

Val Asp Tyr Pro Tyr Ala Ser Asn Phe Leu Gln Pro Leu Pro Ala Trp
290                 295                 300

Pro Ile Lys Val Val Cys Gln Tyr Leu Lys Asn Pro Asn Val Ser Asp
305                 310                 315                 320

Ser Leu Leu Gln Asn Ile Phe Gln Ala Leu Asn Val Tyr Tyr Asn
            325                 330                 335

Tyr Ser Gly Gln Val Lys Cys Leu Asn Ile Ser Glu Thr Ala Thr Ser
        340                 345                 350

Ser Leu Gly Thr Leu Gly Trp Ser Tyr Gln Ala Cys Thr Glu Val Val
    355                 360                 365

Met Pro Phe Cys Thr Asn Gly Val Asp Asp Met Phe Glu Pro His Ser
370                 375                 380

Trp Asn Leu Lys Glu Leu Ser Asp Asp Cys Phe Gln Gln Trp Gly Val
385                 390                 395                 400

Arg Pro Arg Pro Ser Trp Ile Thr Thr Met Tyr Gly Gly Lys Asn Ile
            405                 410                 415

Ser Ser His Thr Asn Ile Val Phe Ser Asn Gly Glu Leu Asp Pro Trp
        420                 425                 430

Ser Gly Gly Gly Val Thr Lys Asp Ile Thr Asp Thr Leu Val Ala Val
    435                 440                 445
```

-continued

```
Thr Ile Ser Glu Gly Ala His His Leu Asp Leu Arg Thr Lys Asn Ala
    450                 455                 460

Leu Asp Pro Met Ser Val Leu Leu Ala Arg Ser Leu Glu Val Arg His
465                 470                 475                 480

Met Lys Asn Trp Ile Arg Asp Phe Tyr Asp Ser Ala Gly Lys Gln His
            485                 490                 495

<210> 2
<211> 710
<212> PRT
<213> NP_002717 PREP

<400> 2

Met Leu Ser Leu Gln Tyr Pro Asp Val Tyr Arg Asp Glu Thr Ala Val
1               5                   10                  15

Gln Asp Tyr His Gly His Lys Ile Cys Asp Pro Tyr Ala Trp Leu Glu
            20                  25                  30

Asp Pro Asp Ser Glu Gln Thr Lys Ala Phe Val Glu Ala Gln Asn Lys
        35                  40                  45

Ile Thr Val Pro Phe Leu Glu Gln Cys Pro Ile Arg Gly Leu Tyr Lys
    50                  55                  60

Glu Arg Met Thr Glu Leu Tyr Asp Tyr Pro Lys Tyr Ser Cys His Phe
65                  70                  75                  80

Lys Lys Gly Lys Arg Tyr Phe Tyr Phe Tyr Asn Thr Gly Leu Gln Asn
            85                  90                  95

Gln Arg Val Leu Tyr Val Gln Asp Ser Leu Glu Gly Glu Ala Arg Val
            100                 105                 110

Phe Leu Asp Pro Asn Ile Leu Ser Asp Gly Thr Val Ala Leu Arg
        115                 120                 125

Gly Tyr Ala Phe Ser Glu Asp Gly Glu Tyr Phe Ala Tyr Gly Leu Ser
    130                 135                 140

Ala Ser Gly Ser Asp Trp Val Thr Ile Lys Phe Met Lys Val Asp Gly
145                 150                 155                 160

Ala Lys Glu Leu Pro Asp Val Leu Glu Arg Val Lys Phe Ser Cys Met
            165                 170                 175

Ala Trp Thr His Asp Gly Lys Gly Met Phe Tyr Asn Ser Tyr Pro Gln
            180                 185                 190

Gln Asp Gly Lys Ser Asp Gly Thr Glu Thr Ser Thr Asn Leu His Gln
        195                 200                 205

Lys Leu Tyr Tyr His Val Leu Gly Thr Asp Gln Ser Glu Asp Ile Leu
    210                 215                 220

Cys Ala Glu Phe Pro Asp Glu Pro Lys Trp Met Gly Gly Ala Glu Leu
225                 230                 235                 240

Ser Asp Asp Gly Arg Tyr Val Leu Leu Ser Ile Arg Glu Gly Cys Asp
            245                 250                 255

Pro Val Asn Arg Leu Trp Tyr Cys Asp Leu Gln Gln Glu Ser Ser Gly
            260                 265                 270

Ile Ala Gly Ile Leu Lys Trp Val Lys Leu Ile Asp Asn Phe Glu Gly
        275                 280                 285

Glu Tyr Asp Tyr Val Thr Asn Glu Gly Thr Val Phe Thr Phe Lys Thr
    290                 295                 300

Asn Arg Gln Ser Pro Asn Tyr Arg Val Ile Asn Ile Asp Phe Arg Asp
305                 310                 315                 320

Pro Glu Glu Ser Lys Trp Lys Val Leu Val Pro Glu His Glu Lys Asp
            325                 330                 335
```

-continued

```
Val Leu Glu Trp Ile Ala Cys Val Arg Ser Asn Phe Leu Val Leu Cys
    340                 345                 350
Tyr Leu His Asp Val Lys Asn Ile Gln Leu His Asp Leu Thr Thr
    355                 360             365
Gly Ala Leu Leu Lys Thr Phe Pro Leu Asp Val Gly Ser Ile Val Gly
    370                 375                 380
Tyr Ser Gly Gln Lys Lys Asp Thr Glu Ile Phe Tyr Gln Phe Thr Ser
385                 390                 395                 400
Phe Leu Ser Pro Gly Ile Ile Tyr His Cys Asp Leu Thr Lys Glu Glu
            405                 410                 415
Leu Glu Pro Arg Val Phe Arg Glu Val Thr Val Lys Gly Ile Asp Ala
        420                 425                 430
Ser Asp Tyr Gln Thr Val Gln Ile Phe Tyr Pro Ser Lys Asp Gly Thr
    435                 440                 445
Lys Ile Pro Met Phe Ile Val His Lys Lys Gly Ile Lys Leu Asp Gly
    450                 455                 460
Ser His Pro Ala Phe Leu Tyr Gly Tyr Gly Gly Phe Asn Ile Ser Ile
465                 470                 475                 480
Thr Pro Asn Tyr Ser Val Ser Arg Leu Ile Phe Val Arg His Met Gly
            485                 490                 495
Gly Ile Leu Ala Val Ala Asn Ile Arg Gly Gly Gly Glu Tyr Gly Glu
        500                 505                 510
Thr Trp His Lys Gly Gly Ile Leu Ala Asn Lys Gln Asn Cys Phe Asp
    515                 520                 525
Asp Phe Gln Cys Ala Ala Glu Tyr Leu Ile Lys Glu Gly Tyr Thr Ser
    530                 535                 540
Pro Lys Arg Leu Thr Ile Asn Gly Gly Ser Asn Gly Gly Leu Leu Val
545                 550                 555                 560
Ala Ala Cys Ala Asn Gln Arg Pro Asp Leu Phe Gly Cys Val Ile Ala
            565                 570                 575
Gln Val Gly Val Met Asp Met Leu Lys Phe His Lys Tyr Thr Ile Gly
        580                 585                 590
His Ala Trp Thr Thr Asp Tyr Gly Cys Ser Asp Ser Lys Gln His Phe
    595                 600                 605
Glu Trp Leu Val Lys Tyr Ser Pro Leu His Asn Val Lys Leu Pro Glu
    610                 615                 620
Ala Asp Asp Ile Gln Tyr Pro Ser Met Leu Leu Thr Ala Asp His
625                 630                 635                 640
Asp Asp Arg Val Val Pro Leu His Ser Leu Lys Phe Ile Ala Thr Leu
            645                 650                 655
Gln Tyr Ile Val Gly Arg Ser Arg Lys Gln Ser Asn Pro Leu Leu Ile
        660                 665                 670
His Val Asp Thr Lys Ala Gly His Gly Ala Gly Lys Pro Thr Ala Lys
    675                 680                 685
Val Ile Glu Glu Val Ser Asp Met Phe Ala Phe Ile Ala Arg Cys Leu
    690                 695                 700
Asn Val Asp Trp Ile Pro
705             710

<210> 3
<211> 23
<212> DNA
<213> PRCP forward primer

<400> 3
tctacactgg taatgaaggg gac                                    23
```

<210> 4
<211> 23
<212> DNA
<213> PRCP reverse primer

<400> 4
tccttgaatg agttgtcacc aaa        23

<210> 5
<211> 21
<212> DNA
<213> PREP forward primer

<400> 5
gagaccgccg tacaggatta t        21

<210> 6
<211> 23
<212> DNA
<213> PREP reverse primer

<400> 6
tgaagtggca actatacttg gga        23

SEQUENCE LISTING

<160> NUMBER OF SEQ ID NOS: 6

<210> SEQ ID NO 1
<211> LENGTH: 496
<212> TYPE: PRT
<213> ORGANISM: Homo sapiens

<400> SEQUENCE: 1

Met Gly Arg Arg Ala Leu Leu Leu Leu Leu Ser Phe Leu Ala Pro
1               5                   10                  15

Trp Ala Thr Ile Ala Leu Arg Pro Ala Leu Arg Ala Leu Gly Ser Leu
                20                  25                  30

His Leu Pro Thr Asn Pro Thr Ser Leu Pro Ala Val Ala Lys Asn Tyr
            35                  40                  45

Ser Val Leu Tyr Phe Gln Gln Lys Val Asp His Phe Gly Phe Asn Thr
    50                  55                  60

Val Lys Thr Phe Asn Gln Arg Tyr Leu Val Ala Asp Lys Tyr Trp Lys
65                  70                  75                  80

Lys Asn Gly Gly Ser Ile Leu Phe Tyr Thr Gly Asn Glu Gly Asp Ile
                85                  90                  95

Ile Trp Phe Cys Asn Asn Thr Gly Phe Met Trp Asp Val Ala Glu Glu
            100                 105                 110

Leu Lys Ala Met Leu Val Phe Ala Glu His Arg Tyr Tyr Gly Glu Ser
            115                 120                 125

Leu Pro Phe Gly Asp Asn Ser Phe Lys Asp Ser Arg His Leu Asn Phe
        130                 135                 140

Leu Thr Ser Glu Gln Ala Leu Ala Asp Phe Ala Glu Leu Ile Lys His
145                 150                 155                 160

Leu Lys Arg Thr Ile Pro Gly Ala Glu Asn Gln Pro Val Ile Ala Ile
                165                 170                 175

Gly Gly Ser Tyr Gly Gly Met Leu Ala Ala Trp Phe Arg Met Lys Tyr
            180                 185                 190

Pro His Met Val Val Gly Ala Leu Ala Ala Ser Ala Pro Ile Trp Gln
        195                 200                 205

Phe Glu Asp Leu Val Pro Cys Gly Val Phe Met Lys Ile Val Thr Thr
    210                 215                 220

```
Asp Phe Arg Lys Ser Gly Pro His Cys Ser Glu Ser Ile His Arg Ser
225                 230                 235                 240

Trp Asp Ala Ile Asn Arg Leu Ser Asn Thr Gly Ser Gly Leu Gln Trp
            245                 250                 255

Leu Thr Gly Ala Leu His Leu Cys Ser Pro Leu Thr Ser Gln Asp Ile
        260                 265                 270

Gln His Leu Lys Asp Trp Ile Ser Glu Thr Trp Val Asn Leu Ala Met
    275                 280                 285

Val Asp Tyr Pro Tyr Ala Ser Asn Phe Leu Gln Pro Leu Pro Ala Trp
290                 295                 300

Pro Ile Lys Val Val Cys Gln Tyr Leu Lys Asn Pro Asn Val Ser Asp
305                 310                 315                 320

Ser Leu Leu Leu Gln Asn Ile Phe Gln Ala Leu Asn Val Tyr Tyr Asn
            325                 330                 335

Tyr Ser Gly Gln Val Lys Cys Leu Asn Ile Ser Glu Thr Ala Thr Ser
        340                 345                 350

Ser Leu Gly Thr Leu Gly Trp Ser Tyr Gln Ala Cys Thr Glu Val Val
    355                 360                 365

Met Pro Phe Cys Thr Asn Gly Val Asp Asp Met Phe Glu Pro His Ser
370                 375                 380

Trp Asn Leu Lys Glu Leu Ser Asp Asp Cys Phe Gln Gln Trp Gly Val
385                 390                 395                 400

Arg Pro Arg Pro Ser Trp Ile Thr Thr Met Tyr Gly Gly Lys Asn Ile
            405                 410                 415

Ser Ser His Thr Asn Ile Val Phe Ser Asn Gly Glu Leu Asp Pro Trp
        420                 425                 430

Ser Gly Gly Gly Val Thr Lys Asp Ile Thr Asp Thr Leu Val Ala Val
    435                 440                 445

Thr Ile Ser Glu Gly Ala His His Leu Asp Leu Arg Thr Lys Asn Ala
450                 455                 460

Leu Asp Pro Met Ser Val Leu Leu Ala Arg Ser Leu Glu Val Arg His
465                 470                 475                 480

Met Lys Asn Trp Ile Arg Asp Phe Tyr Asp Ser Ala Gly Lys Gln His
            485                 490                 495

<210> SEQ ID NO 2
<211> LENGTH: 710
<212> TYPE: PRT
<213> ORGANISM: Homo sapiens

<400> SEQUENCE: 2

Met Leu Ser Leu Gln Tyr Pro Asp Val Tyr Arg Asp Glu Thr Ala Val
1               5                   10                  15

Gln Asp Tyr His Gly His Lys Ile Cys Asp Pro Tyr Ala Trp Leu Glu
            20                  25                  30

Asp Pro Asp Ser Glu Gln Thr Lys Ala Phe Val Glu Ala Gln Asn Lys
        35                  40                  45

Ile Thr Val Pro Phe Leu Glu Gln Cys Pro Ile Arg Gly Leu Tyr Lys
    50                  55                  60

Glu Arg Met Thr Glu Leu Tyr Asp Tyr Pro Lys Tyr Ser Cys His Phe
65                  70                  75                  80

Lys Lys Gly Lys Arg Tyr Phe Tyr Phe Tyr Asn Thr Gly Leu Gln Asn
            85                  90                  95

Gln Arg Val Leu Tyr Val Gln Asp Ser Leu Glu Gly Glu Ala Arg Val
```

```
                100             105             110
Phe Leu Asp Pro Asn Ile Leu Ser Asp Asp Gly Thr Val Ala Leu Arg
            115             120             125
Gly Tyr Ala Phe Ser Glu Asp Gly Glu Tyr Phe Ala Tyr Gly Leu Ser
            130             135             140
Ala Ser Gly Ser Asp Trp Val Thr Ile Lys Phe Met Lys Val Asp Gly
145             150             155             160
Ala Lys Glu Leu Pro Asp Val Leu Glu Arg Val Lys Phe Ser Cys Met
            165             170             175
Ala Trp Thr His Asp Gly Lys Gly Met Phe Tyr Asn Ser Tyr Pro Gln
            180             185             190
Gln Asp Gly Lys Ser Asp Gly Thr Glu Thr Ser Thr Asn Leu His Gln
            195             200             205
Lys Leu Tyr Tyr His Val Leu Gly Thr Asp Gln Ser Glu Asp Ile Leu
            210             215             220
Cys Ala Glu Phe Pro Asp Glu Pro Lys Trp Met Gly Gly Ala Glu Leu
225             230             235             240
Ser Asp Asp Gly Arg Tyr Val Leu Leu Ser Ile Arg Glu Gly Cys Asp
            245             250             255
Pro Val Asn Arg Leu Trp Tyr Cys Asp Leu Gln Gln Glu Ser Ser Gly
            260             265             270
Ile Ala Gly Ile Leu Lys Trp Val Lys Leu Ile Asp Asn Phe Glu Gly
            275             280             285
Glu Tyr Asp Tyr Val Thr Asn Glu Gly Thr Val Phe Thr Phe Lys Thr
            290             295             300
Asn Arg Gln Ser Pro Asn Tyr Arg Val Ile Asn Ile Asp Phe Arg Asp
305             310             315             320
Pro Glu Glu Ser Lys Trp Lys Val Leu Val Pro Glu His Glu Lys Asp
            325             330             335
Val Leu Glu Trp Ile Ala Cys Val Arg Ser Asn Phe Leu Val Leu Cys
            340             345             350
Tyr Leu His Asp Val Lys Asn Ile Leu Gln Leu His Asp Leu Thr Thr
            355             360             365
Gly Ala Leu Leu Lys Thr Phe Pro Leu Asp Val Gly Ser Ile Val Gly
            370             375             380
Tyr Ser Gly Gln Lys Lys Asp Thr Glu Ile Phe Tyr Gln Phe Thr Ser
385             390             395             400
Phe Leu Ser Pro Gly Ile Ile Tyr His Cys Asp Leu Thr Lys Glu Glu
            405             410             415
Leu Glu Pro Arg Val Phe Arg Glu Val Thr Val Lys Gly Ile Asp Ala
            420             425             430
Ser Asp Tyr Gln Thr Val Gln Ile Phe Tyr Pro Ser Lys Asp Gly Thr
            435             440             445
Lys Ile Pro Met Phe Ile Val His Lys Gly Ile Lys Leu Asp Gly
            450             455             460
Ser His Pro Ala Phe Leu Tyr Gly Tyr Gly Gly Phe Asn Ile Ser Ile
465             470             475             480
Thr Pro Asn Tyr Ser Val Ser Arg Leu Ile Phe Val Arg His Met Gly
            485             490             495
Gly Ile Leu Ala Val Ala Asn Ile Arg Gly Gly Gly Glu Tyr Gly Glu
            500             505             510
Thr Trp His Lys Gly Gly Ile Leu Ala Asn Lys Gln Asn Cys Phe Asp
            515             520             525
```

Asp Phe Gln Cys Ala Ala Glu Tyr Leu Ile Lys Glu Gly Tyr Thr Ser
            530                 535                 540

Pro Lys Arg Leu Thr Ile Asn Gly Gly Ser Asn Gly Gly Leu Leu Val
545                 550                 555                 560

Ala Ala Cys Ala Asn Gln Arg Pro Asp Leu Phe Gly Cys Val Ile Ala
                565                 570                 575

Gln Val Gly Val Met Asp Met Leu Lys Phe His Lys Tyr Thr Ile Gly
            580                 585                 590

His Ala Trp Thr Thr Asp Tyr Gly Cys Ser Asp Ser Lys Gln His Phe
        595                 600                 605

Glu Trp Leu Val Lys Tyr Ser Pro Leu His Asn Val Lys Leu Pro Glu
    610                 615                 620

Ala Asp Asp Ile Gln Tyr Pro Ser Met Leu Leu Thr Ala Asp His
625                 630                 635                 640

Asp Asp Arg Val Val Pro Leu His Ser Leu Lys Phe Ile Ala Thr Leu
                645                 650                 655

Gln Tyr Ile Val Gly Arg Ser Arg Lys Gln Ser Asn Pro Leu Leu Ile
            660                 665                 670

His Val Asp Thr Lys Ala Gly His Gly Ala Gly Lys Pro Thr Ala Lys
        675                 680                 685

Val Ile Glu Glu Val Ser Asp Met Phe Ala Phe Ile Ala Arg Cys Leu
    690                 695                 700

Asn Val Asp Trp Ile Pro
705                 710

<210> SEQ ID NO 3
<211> LENGTH: 23
<212> TYPE: DNA
<213> ORGANISM: Artificial Sequence
<220> FEATURE:
<223> OTHER INFORMATION: Synthetic DNA Sequence

<400> SEQUENCE: 3
tctacactgg taatgaaggg gac                                             23

<210> SEQ ID NO 4
<211> LENGTH: 23
<212> TYPE: DNA
<213> ORGANISM: Artificial Sequence
<220> FEATURE:
<223> OTHER INFORMATION: Synthetic DNA sequence

<400> SEQUENCE: 4
tccttgaatg agttgtcacc aaa                                             23

<210> SEQ ID NO 5
<211> LENGTH: 21
<212> TYPE: DNA
<213> ORGANISM: Artificial Sequence
<220> FEATURE:
<223> OTHER INFORMATION: Synthetic DNA sequence

<400> SEQUENCE: 5
gagaccgccg tacaggatta t                                               21

<210> SEQ ID NO 6
<211> LENGTH: 23
<212> TYPE: DNA
<213> ORGANISM: Artificial Sequence
<220> FEATURE:

-continued

```
<223> OTHER INFORMATION: Synthetic DNA sequence

<400> SEQUENCE: 6
tgaagtggca actatacttg gga                                          23
```

The invention claimed is:

1. A method for treating cancer, said method comprising administering to a patient in need of the treatment an effective dose of the PRCP and PREP dual antagonist [2-[8-(dimethylamino)octylsulfanyl]-6-propan-2-ylpyridin-3-yl]thiophen-2-ylmethanone (Y29794).

2. The method of claim 1, wherein the method further comprises administering to the patient an effective amount of an mTOR antagonist.

3. The method of claim 2, wherein the mTOR antagonist is rapamycin.

* * * * *

UNITED STATES PATENT AND TRADEMARK OFFICE
CERTIFICATE OF CORRECTION

PATENT NO. : 9,545,396 B2
APPLICATION NO. : 14/431441
DATED : January 17, 2017
INVENTOR(S) : Lei Duan et al.

Page 1 of 1

It is certified that error appears in the above-identified patent and that said Letters Patent is hereby corrected as shown below:

In the Claims

Column 35, Line 13, Claim 1: Please delete "[2-[8- (dimethylamino)octylsulfanyl]-6-propan-2-ylpyridin-3-yl]thiophen-2-ylmethanone" and insert --[2-[8- (dimethylamino)octylsulfanyl]-6-propan-2-ylpyridin-3-yl]-thiophen-2-ylmethanone--

Signed and Sealed this
Twenty-ninth Day of August, 2017

Joseph Matal
*Performing the Functions and Duties of the*
*Under Secretary of Commerce for Intellectual Property and*
*Director of the United States Patent and Trademark Office*